US009603999B2

(12) United States Patent
Hungerford et al.

(10) Patent No.: US 9,603,999 B2
(45) Date of Patent: Mar. 28, 2017

(54) INFUSION SYSTEM USING OPTICAL IMAGER FOR CONTROLLING FLOW AND METHOD THEREOF

(71) Applicants: BAXTER INTERNATIONAL INC., Deerfield, IL (US); BAXTER HEALTHCARE S.A., Glattpark (Opfikon) (CH)

(72) Inventors: Roger L. Hungerford, Medina, NY (US); Tuan Bui, Buffalo, NY (US)

(73) Assignees: BAXTER INTERNATIONAL INC., Deerfield, IL (US); BAXTER HEALTHCARE S.A., Glattpark (Opfikon) (CH)

( * ) Notice: Subject to any disclaimer, the term of this patent is extended or adjusted under 35 U.S.C. 154(b) by 427 days.

(21) Appl. No.: 14/086,561

(22) Filed: Nov. 21, 2013

(65) Prior Publication Data

US 2014/0081233 A1  Mar. 20, 2014

Related U.S. Application Data

(63) Continuation of application No. 12/907,403, filed on Oct. 19, 2010, now Pat. No. 8,622,979.

(51) Int. Cl.
*A61M 5/14* (2006.01)
*A61M 5/168* (2006.01)

(52) U.S. Cl.
CPC ... *A61M 5/1689* (2013.01); *A61M 2205/3306* (2013.01)

(58) Field of Classification Search
CPC ............... A61M 5/1689; A61M 5/168; A61M 2205/3306
(Continued)

(56) References Cited

U.S. PATENT DOCUMENTS 3,609,379 A   9/1971 Hildebrandt
4,105,028 A * 8/1978 Sadlier et al. ................. 604/65
(Continued)

FOREIGN PATENT DOCUMENTS

DE    3617723    12/1987
WO    9309407     5/1993
(Continued)

OTHER PUBLICATIONS

Luerkens, "Theory and Application of Morphological Analysis, Fine Particles and Surfaces", CRC Press, 1991, pp. 5-7.
(Continued)

*Primary Examiner* — Edelmira Bosques
(74) *Attorney, Agent, or Firm* — Greer, Burns & Crain, Ltd.

(57) ABSTRACT

A method of operating an infusion pump includes transmitting light through or around a drop of fluid suspended from an end of a drip tube for the infusion pump, the end of the drip tube located in a drip chamber for the infusion pump, wherein the drip tube is configured for connection to a source of the fluid; receiving, using an optical system for the pump, light transmitted through or around the drop; transmitting, to a specially programmed microprocessor and using the optical system, data regarding the received light; and, using the microprocessor to calculate a volume of the drop using the data.

13 Claims, 16 Drawing Sheets

(58) Field of Classification Search
USPC .......................................................... 604/251
See application file for complete search history.

(56) References Cited

U.S. PATENT DOCUMENTS

| | | | |
|---|---|---|---|
| 4,321,461 A | 3/1982 | Walter, Jr. et al. | |
| 4,328,801 A | 5/1982 | Marx et al. | |
| 4,504,263 A | 3/1985 | Steuer et al. | |
| 4,525,163 A | 6/1985 | Slavik et al. | |
| 4,583,975 A | 4/1986 | Pekkarinen et al. | |
| 4,634,426 A | 1/1987 | Kamen | |
| 4,673,820 A | 6/1987 | Kamen | |
| 4,680,977 A | 7/1987 | Conero et al. | |
| 4,703,314 A | 10/1987 | Spani | |
| 4,718,896 A | 1/1988 | Arndt et al. | |
| 4,820,281 A | 4/1989 | Lawler, Jr. | |
| 4,909,786 A | 3/1990 | Gijselhart et al. | |
| 4,936,828 A | 6/1990 | Chiang | |
| 5,045,069 A | 9/1991 | Imparato | |
| 5,057,090 A | 10/1991 | Bessman | |
| 5,186,057 A | 2/1993 | Everhart | |
| 5,267,980 A | 12/1993 | Dirr, Jr. et al. | |
| 5,331,309 A | 7/1994 | Sakai | |
| 5,415,641 A | 5/1995 | Yerlikaya et al. | |
| 5,562,615 A | 10/1996 | Nassif | |
| 5,588,963 A | 12/1996 | Roelofs | |
| 5,896,195 A * | 4/1999 | Juvinall et al. | 356/240.1 |
| 5,899,665 A | 5/1999 | Makino et al. | |
| 6,049,381 A | 4/2000 | Reintjes et al. | |
| 6,083,206 A | 7/2000 | Molko | |
| 6,144,453 A * | 11/2000 | Hallerman et al. | 356/616 |
| 6,149,631 A | 11/2000 | Haydel, Jr. | |
| 6,159,186 A | 12/2000 | Wickham et al. | |
| 6,213,354 B1 | 4/2001 | Kay | |
| 6,562,012 B1 | 5/2003 | Brown et al. | |
| 6,599,282 B2 | 7/2003 | Burko | |
| 6,736,801 B1 | 5/2004 | Gallagher | |
| 6,984,052 B1 | 1/2006 | Del Castillo | |
| 7,190,275 B2 | 3/2007 | Goldberg et al. | |
| 7,695,448 B2 | 4/2010 | Cassidy et al. | |
| 7,767,991 B2 | 8/2010 | Sacchetti | |
| 7,892,204 B2 | 2/2011 | Kraus | |
| 7,918,834 B2 | 4/2011 | Mernoe et al. | |
| 2003/0045840 A1 | 3/2003 | Burko | |
| 2006/0291211 A1 | 12/2006 | Rodriguez et al. | |
| 2008/0004574 A1 | 1/2008 | Dyar et al. | |
| 2008/0051732 A1 | 2/2008 | Chen | |
| 2010/0309005 A1 | 12/2010 | Warner et al. | |
| 2012/0013735 A1 | 1/2012 | Tao | |

FOREIGN PATENT DOCUMENTS

| | | |
|---|---|---|
| WO | 02/40084 | 5/2002 |
| WO | 2009039203 | 3/2009 |

OTHER PUBLICATIONS

Zbigniew Darzynkiewicz, "Cytometry", Third Edition 2001, vol. 63, pp. 44-46.

* cited by examiner

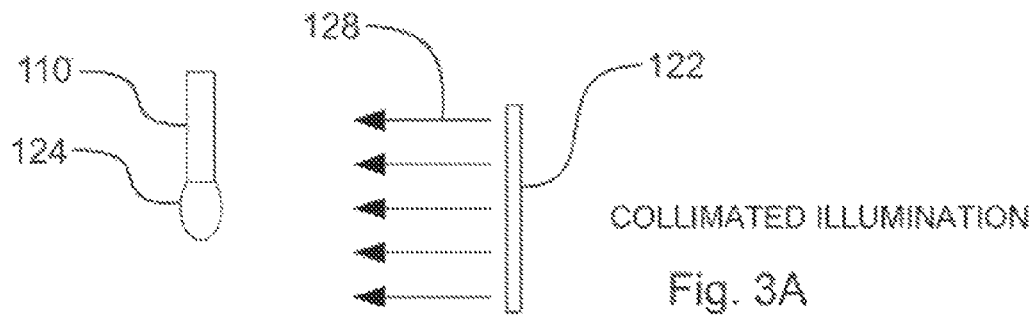
Fig. 3A COLLIMATED ILLUMINATION
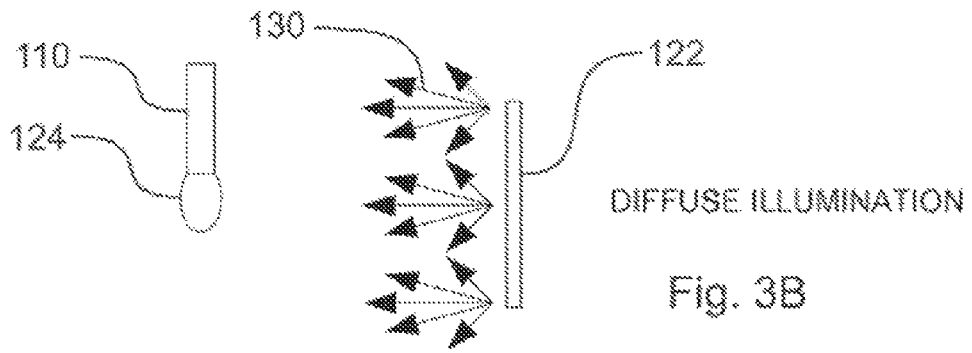
Fig. 3B DIFFUSE ILLUMINATION
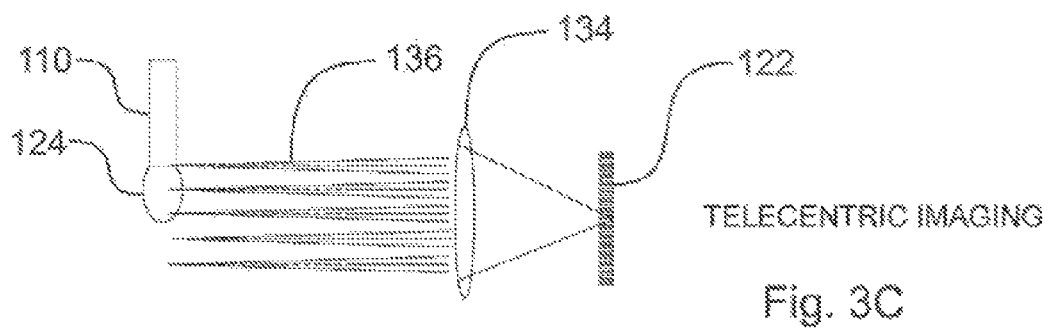
Fig. 3C TELECENTRIC IMAGING
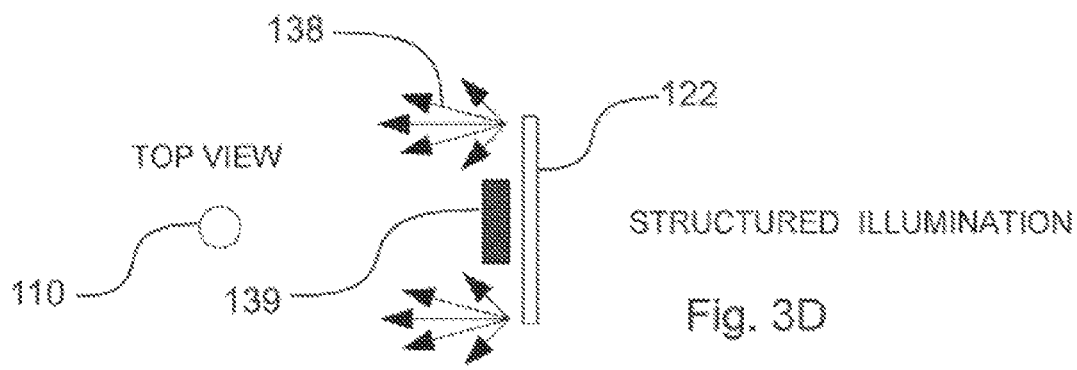
Fig. 3D STRUCTURED ILLUMINATION

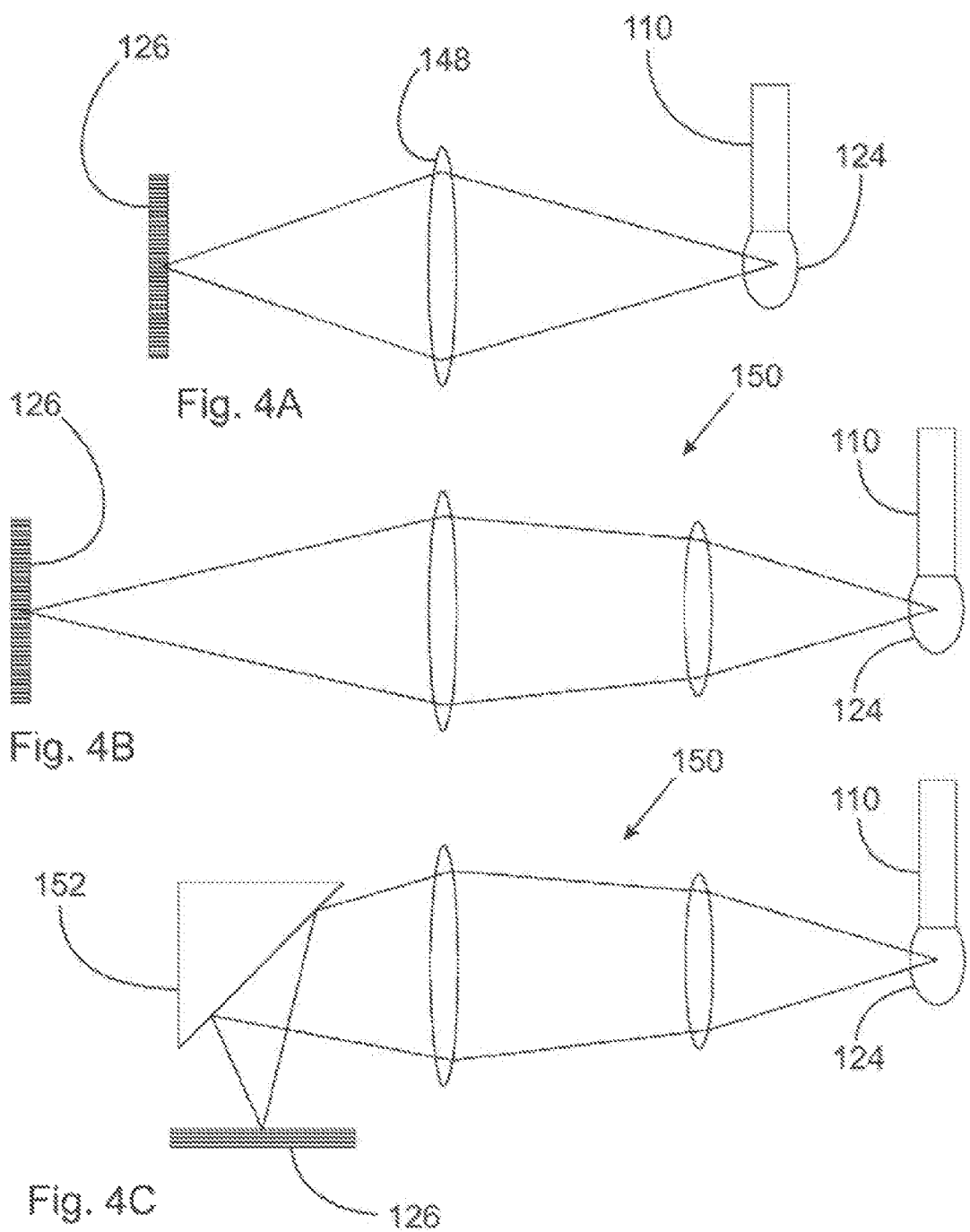

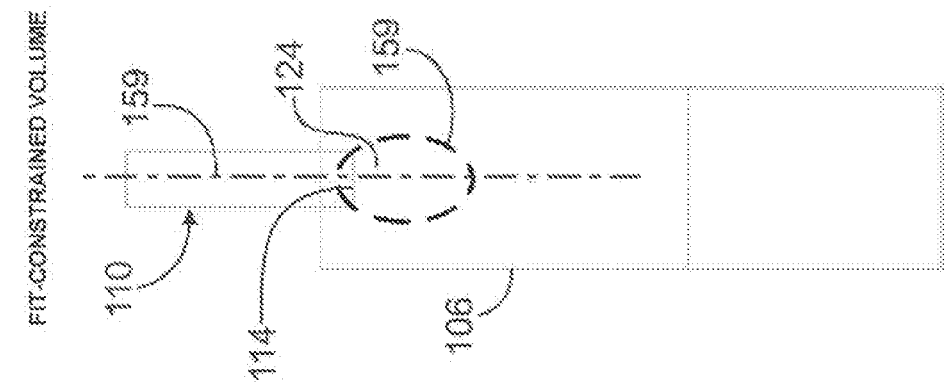
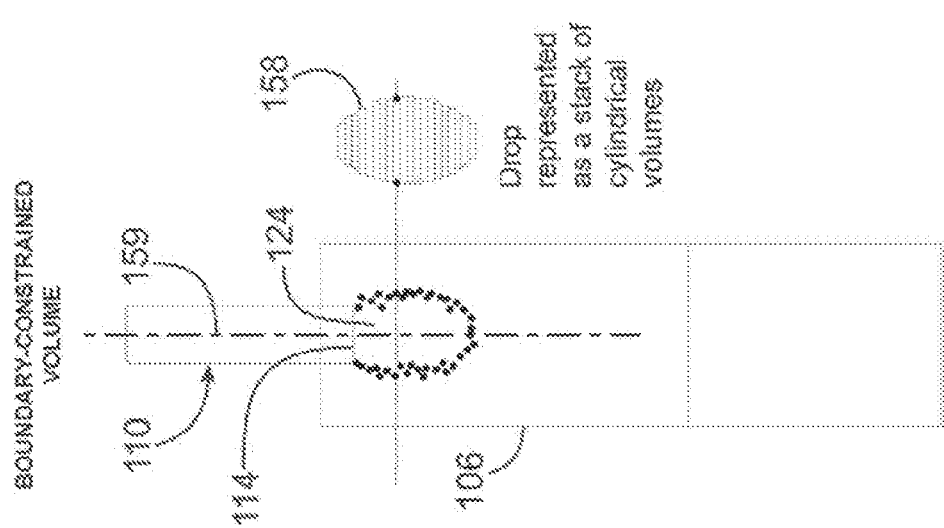
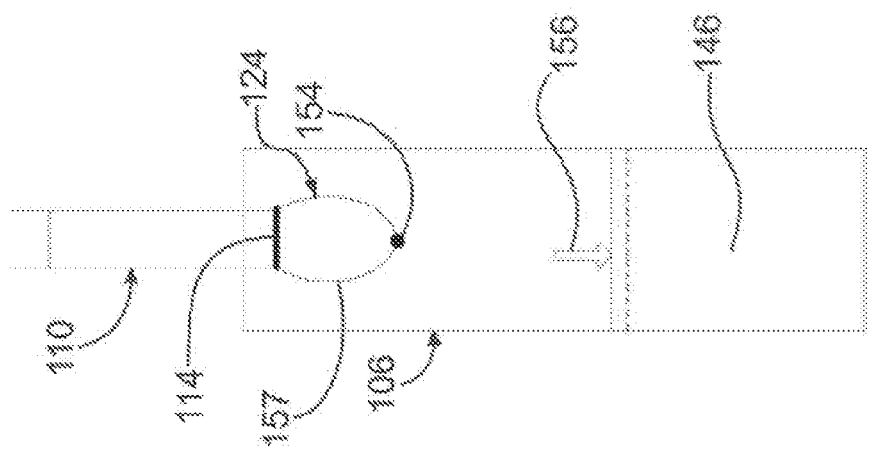

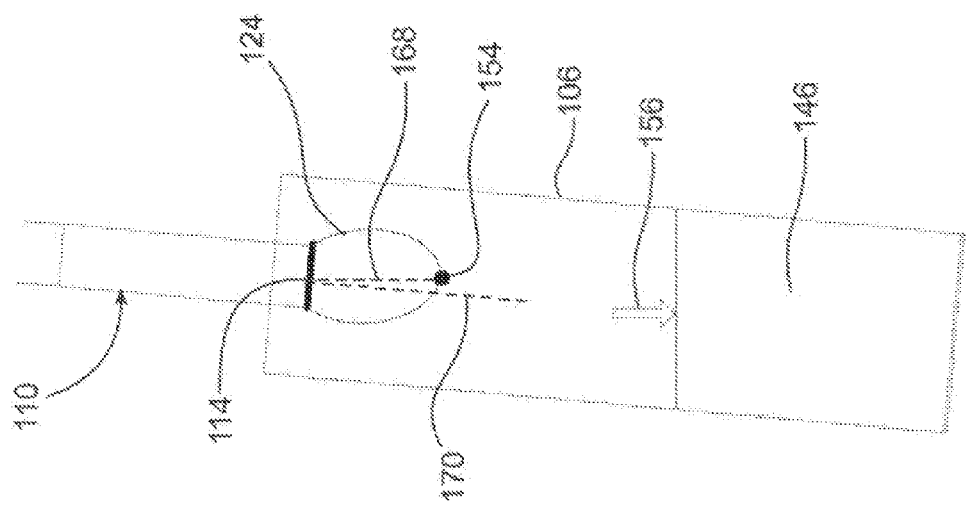
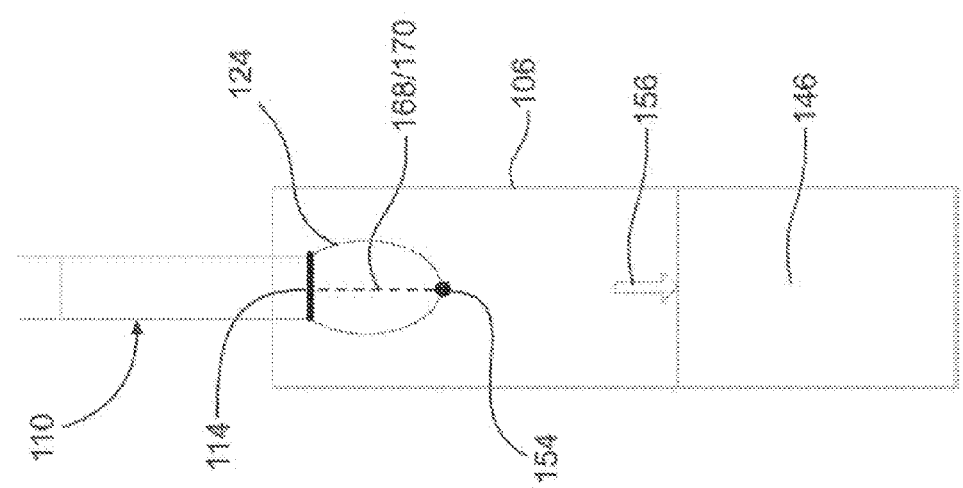

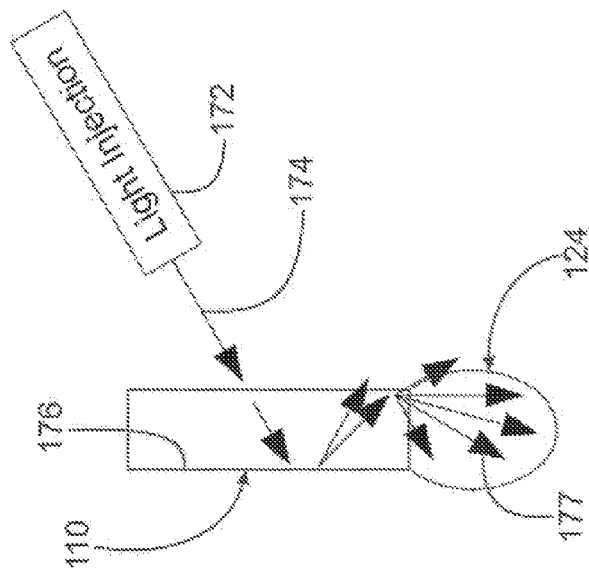
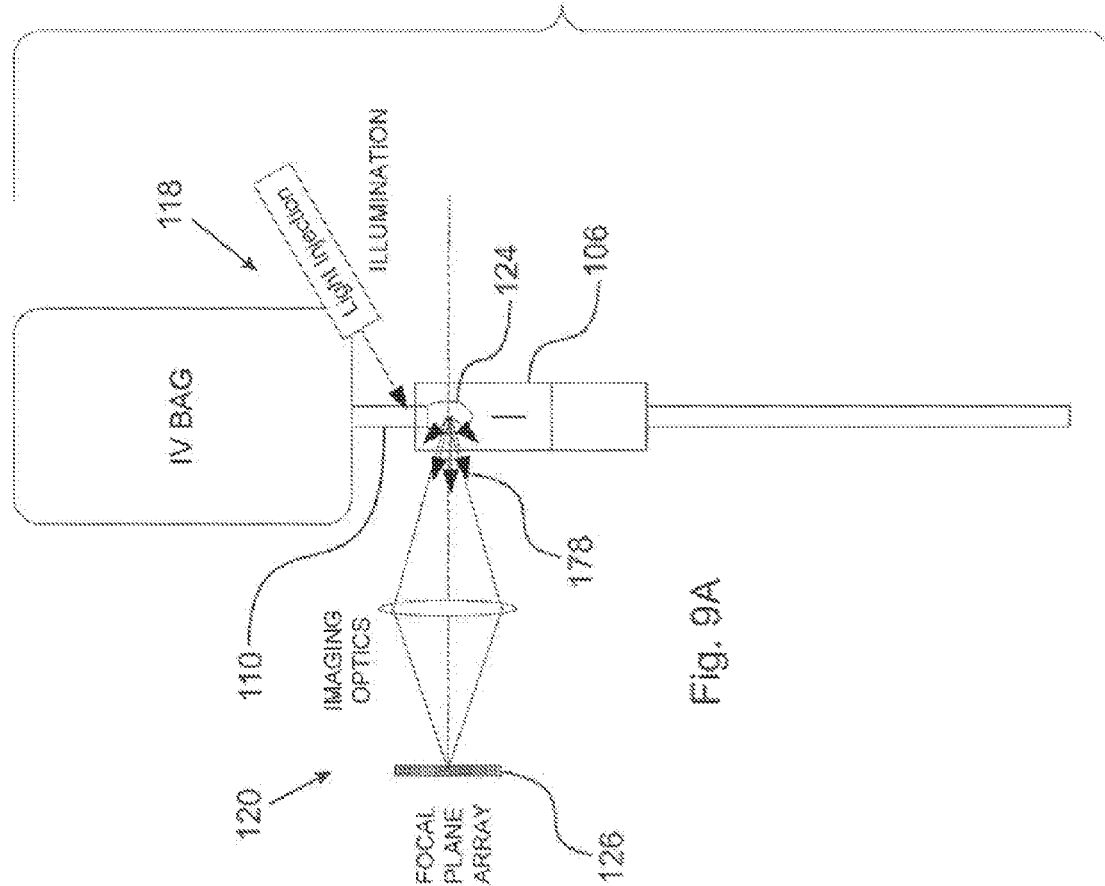
Fig. 9A
Fig. 9B

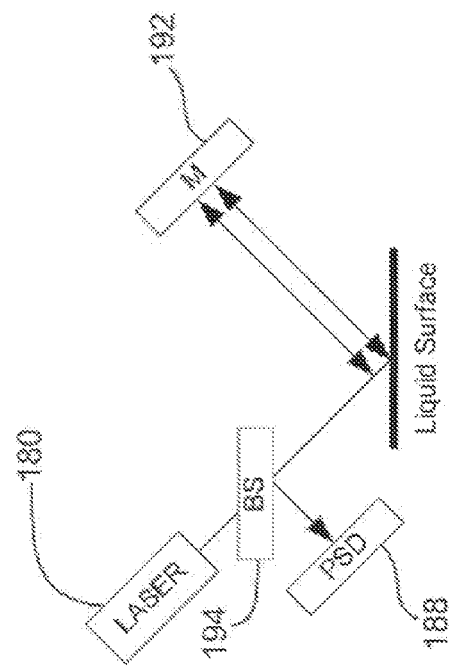
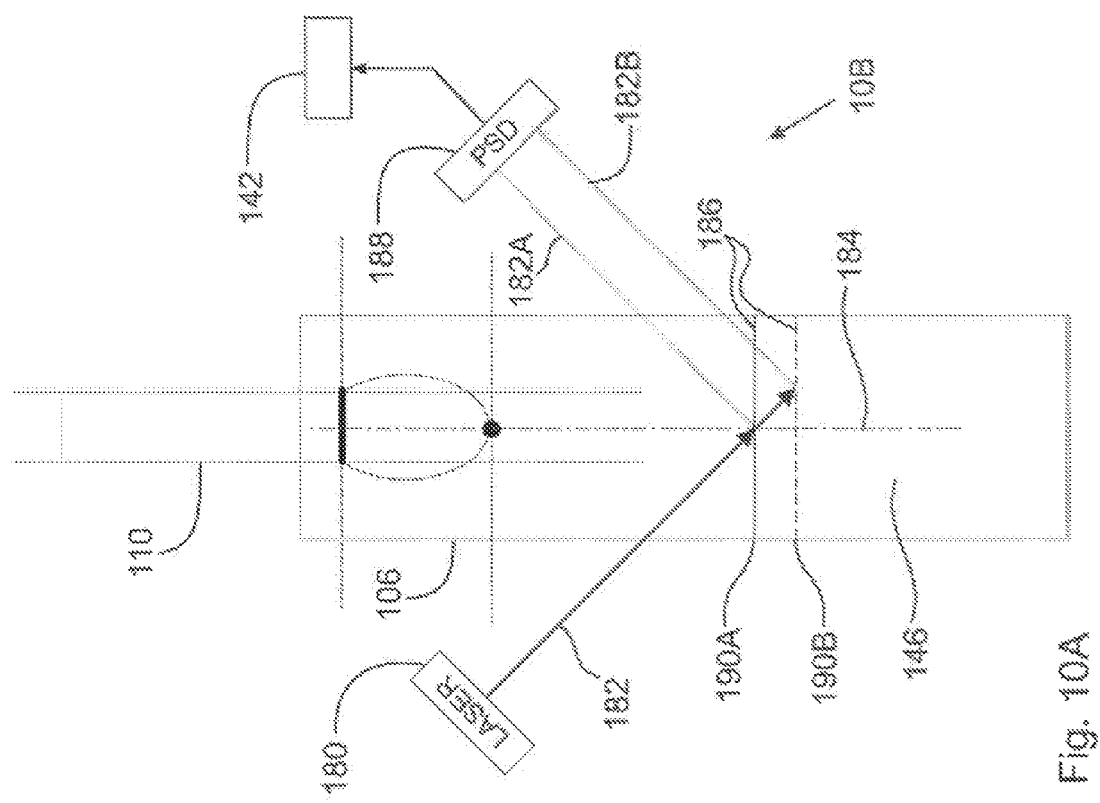
Fig. 10A
Fig. 10B

INFUSION SYSTEM USING OPTICAL IMAGER FOR CONTROLLING FLOW AND METHOD THEREOF

RELATED APPLICATION

This application is a continuation of, and claims 35 USC 120 priority from, U.S. patent application Ser. No. 12/907,403, filed Oct. 19, 2010.

BACKGROUND

The present disclosure relates generally to a pump with optical imaging for calculating drop size and flow rate and for use in pump control and alarm operations.

Prior art references, such as U.S. Pat. No. 4,936,828 (Chiang, Kophu), U.S. Pat. No. 5,588,963 (Roelofs; Bernardus J. G. M.), and U.S. Pat. No. 6,213,354 (Kay, Robert L.) teach respective infusion systems which use optical systems to measure the volume of falling drops. That is, the principle of operation set forth in the prior art, and in the preceding references in particular, is necessarily connected to operations upon a drop that is in free fall through a drip chamber.

SUMMARY

The invention broadly comprises an infusion pump, including: a first specially programmed microprocessor; a drip chamber for connection to an output tube; a drip tube for connection to a source of fluid and with an end disposed in the drip chamber; and an illumination system: with a light source for transmitting light through a wall of the drip chamber to a drop of fluid suspended from the end of the drip tube; and for controlling illumination properties of the light transmitted to the drop. The pump also includes an optical system for: receiving light transmitted through the drop; and transmitting, to the first microprocessor, data regarding the received light. The first microprocessor is for: generating, using the data, an image of the drop; locating, using the image, an outer edge of the drop to define a boundary of the drop; integrating an area enclosed by the boundary; and calculating a volume of revolution for the drop with respect to an axis for the drop that intersects the end of the drip tube, assuming symmetry of the drop with respect to the axis.

The invention broadly comprises an infusion pump, including: a specially programmed microprocessor; a drip chamber for connection to an output tube; a drip tube for connecting the drip chamber to a source of fluid, the drip tube including an end disposed within the drip chamber; an illumination system including a lighting element for transmitting light through or around a drop of fluid hanging from the end of the drip tube; and an optical system for receiving light transmitted through or around the drop and transmitting, to the microprocessor, data regarding the received light. The illumination system includes one of a telecentric lighting element, a structured lighting element, a pair of laser light sources disposed at an acute angle with respect to each other and for generating respective light beams that interact to form an interference pattern, or a projection lens with a pattern in or on a surface of the lens and through which the lighting element transmits light to project the pattern onto the drop. The telecentric lighting element includes a telecentric lens and a first light source and the telecentric lens bundles light rays from the first light source and directs the bundled light rays toward the drop. The structured lighting element includes a second light source and a structural element placed between the second light source and the drop to block or alter light emanating from the second light source. The microprocessor is for calculating a volume of the drop using the data.

The invention broadly comprises an infusion pump, including: a specially programmed microprocessor; a drip chamber for connection to an output tube; a drip tube for connecting the drip chamber to a source of fluid, the drip tube including an end disposed within the drip chamber; and an illumination system, including a light source for transmitting light into the drip tube such that: the light reflects off a plurality of portions of an internally facing surface of the drip tube; and the reflected light is transmitted through the end of the drip tube into an interior of a drop of the fluid hanging from the end of the drip tube such that the interior of the drop is uniformly illuminated. The pump also includes an optical system for receiving light transmitted from the interior of the drop and transmitting, to the microprocessor, data regarding the received light. The microprocessor is for calculating, a volume of the drop using the data.

The invention broadly comprises an infusion pump, including: a specially programmed microprocessor; a drip chamber for connection to a source of fluid and an output tube; and an illumination system including a light source for transmitting light, at an acute angle with respect to a longitudinal axis for the drip chamber, into the drip chamber such that the light reflects, at the acute angle, off a surface of the fluid pooled within the drip chamber. The pump also includes an optical system for receiving light reflected off the surface and transmitting, to the microprocessor, data regarding the received light. The microprocessor is for calculating a position of the surface using the data regarding the received light.

The invention broadly comprises an infusion pump, including: an illumination system; an optical system; and a specially programmed microprocessor. The illumination system is for: illuminating an end of a drip tube located within a drip chamber of the infusion pump, the drip tube for connecting the drip chamber to a source of fluid; and illuminating a drop of the fluid hanging from the end of the drip tube. The optical system is for: receiving first light emanating from the end of the drip tube and second light emanating from the drop and transmitting data regarding the received light to the microprocessor. The microprocessor is for: generating respective images of the drop and the end of the drip tube from the data; locating an apex of the drop from the image, the apex being a portion of the drop at a furthest distance from the end of the drip tube; determining, using the location of the apex, an orientation of the drop with respect to the end of the drip tube; and calculating, using the orientation of the drop with respect to the end of the drip tube, an orientation of the drip chamber.

The invention broadly comprises an infusion pump, including: a specially programmed microprocessor; a drip chamber for connection to an output tube; a drip tube for connecting the drip chamber to a source of fluid, the drip tube including an end disposed within the drip chamber; and an illumination system: including a light source for transmitting light through the wall of the drip chamber to a drop of fluid suspended from the first end of the drip tube; and for controlling the illumination properties of the light transmitted to the drop. The pump also includes an optical system for: receiving light transmitted through the drop; and transmitting data regarding the received light to the microprocessor. The microprocessor is for: generating respective images of the drop and the end of the drip tube from the data; calculating, using the respective images, a boundary of the end of the drip tube; and using the boundary as a reference plane for calculating a volume, shape, or location of the drop.

The invention broadly comprises an infusion pump, including: a microprocessor; a drip chamber for connection to an output tube; a drip tube for connection to a source of fluid and with an end disposed in the drip chamber; and an illumination system: including a light source for transmitting light through the wall of the drip chamber to the end of the drip tube or proximate the end of the drip tube; and for controlling the illumination properties of the transmitted light. The pump also includes an optical system for: receiving light transmitted through the end of the drip tube or proximate the end of the drip tube; and transmitting, to the microprocessor, data regarding the received light. The microprocessor is for: generating an image of the end of the drip tube from the data; determining that a drop of the fluid is absent from the end of the drip tube for a specified period of time; and generating an empty bag alarm or an air-in-line alarm.

The invention broadly comprises an infusion pump, including: a specially programmed microprocessor; a drip chamber for connection to an output tube; a drip tube for connection to a source of fluid and with an end disposed in the drip chamber; and an illumination system: including a light source for transmitting light through the wall of the drip chamber to a drop of fluid suspended from the first end of the drip tube; and for controlling the illumination properties of the transmitted light. The pump also includes an optical imaging system for: receiving light transmitted through the drop; and transmitting, to the microprocessor, data regarding the received light. The microprocessor is for: creating a plurality of temporally successive images of the drop from the data; calculating a respective volume for the drop in each successive image; identifying changes in the respective volumes; and calculating a flow rate of fluid to the output tube based on the changes in the respective volumes.

The invention broadly comprises an infusion pump, including: a specially programmed microprocessor; a drip chamber for connection to an output tube; a drip tube for connection to a source of fluid and with an end disposed in the drip chamber; and an illumination system: including a light source for transmitting light through a wall of the drip chamber to a drop of fluid suspended from the end of the drip tube; and for controlling the illumination properties of the transmitted light. The pump also includes an optical imaging system for: receiving light transmitted through the drop; and transmitting, to the microprocessor, data regarding the received light; and a pumping mechanism acting on the output tube to displace fluid from the drip chamber through the output tube. The microprocessor is for: creating a plurality of temporally successive images of the drop from the data; calculating a respective size for the drop in each successive image; identifying changes in the respective sizes; calculating a flow rate of fluid to the output tube based on the changes in the respective sizes; and controlling the pumping mechanism to match the flow rate of fluid with a desired flow rate of fluid.

The invention broadly comprises a dual infusion pump configuration, including: a specially programmed microprocessor; first and second drip chambers for connection to first and second output tubes, respectively; first and second drip tubes for connection to first and second sources of fluids, respectively, and with first and second ends disposed in the first and second drip chambers, respectively; and first and second illumination systems: including first and second light source for transmitting first and second light through walls of the first and second drip chambers, respectively, to drops of the first and second fluids, suspended from the first and second ends of the first and second drip tubes, respectively; and for controlling first and second illumination properties of the first and second light transmitted to the drops of the first and second fluids, respectively. The configuration also includes: first and second optical systems for: receiving first and second light transmitted through the drops of the first and second fluids, respectively; and transmitting, to the microprocessor, first and second data regarding the first and second received light; and first and second pumping mechanisms for acting on the first and second output tubes to displace first and second fluid from the first and second drip chambers through the first and second output tubes, respectively. The microprocessor is for: operating the first pumping mechanism to generate a first flow rate for the first fluid from the first drip chamber through the first output tube; creating, from the first data, a plurality of temporally successive images of the drop of the first fluid; determining, using the first plurality of temporally successive images, that the first source of fluid is empty when the drop of the first fluid is absent from the first end of the first drip tube for a specified period of time; and operating the second pumping mechanism to generate a second flow rate for the second source of fluid from the second drip chamber through the second output tube in response to determining that the first source of fluid is empty.

The invention broadly comprises a method for operating an infusion pump, including: transmitting light through a wall of a drip chamber for the infusion pump to a drop of fluid suspended from an end of a drip tube for the infusion pump, the drip tube being for connection to a source of fluid and the end of the drip tube being disposed in the drip chamber; controlling, using an illumination system for the infusion pump, illumination properties of the light transmitted to the drop; receiving, using an optical system for the pump, light transmitted through the drop; detecting, using the optical system, an image; transmitting, to a first specially programmed microprocessor and using the optical system, data regarding the image; and using the first microprocessor to: locate, from the data, an outer edge of the drop to define a boundary of the drop; integrate an area enclosed by the boundary; and calculate a volume of revolution for the drop with respect to an axis for the drop that intersects the end of the drip tube, assuming symmetry of the drop with respect to the axis.

The invention broadly comprises a method for operating an infusion pump, including: transmitting light through or around a drop of fluid suspended from an end of a drip tube for the infusion pump, the end of the drip tube located in a drip chamber for the infusion pump, the drip tube being for connection to a source of the fluid; receiving, using an optical system for the pump, light transmitted through or around the drop; transmitting, to a specially programmed microprocessor and using the optical system, data regarding the received light; and using the microprocessor to calculate a volume of the drop using the data. Transmitting light includes: using a telecentric lighting element including a telecentric lens and a first light source, the telecentric lens bundling light rays from the first light source and directing the bundled light rays toward the drop; using a structured lighting element including a second light source and a structural element placed between the second light source and the drop to block or alter light emanating from the second light source; using a pair of laser light sources disposed at an acute angle with respect to each other to generate respective light beams that interact to form an interference pattern; or transmitting light through a projection lens, the lens having a pattern in or on a surface of the lens, to project the pattern onto the drop.

The invention broadly comprises a method for operating an infusion pump, including: transmitting light into a drip tube for the infusion pump, an end of the drip tube disposed in a drip chamber for the infusion pump such that: the light reflects off a plurality of portions of an internally facing surface of the drip tube; and the reflected light is transmitted through the end of the drip tube into an interior of a drop of fluid hanging from the end of the drip tube such that the interior of the drop is uniformly illuminated, wherein the drip tube is for connection to a source of the fluid. The method also includes: receiving, using an optical system for the pump, light transmitted from the interior of the drop; transmitting, to a specially programmed microprocessor and using the optical system, data regarding the received light; and calculating, using the microprocessor, a volume of the drop using the data.

The invention broadly comprises a method for operating an infusion pump, including: transmitting light, at an acute angle with respect to a longitudinal axis for a drip chamber for the infusion pump, into the drip chamber such that the light reflects, at the acute angle, off a surface of fluid pooled within the drip chamber; receiving, using an optical system for the pump, light reflected from the surface; transmitting, to a specially programmed microprocessor and using the optical system, data regarding the received light; and calculating, using the processor, a position of the surface using the data regarding the received light.

The invention broadly comprises a method for operating an infusion pump, including: illuminating, using an illumination system for the infusion pump, an end of a drip tube located within a drip chamber of the infusion pump, the drip tube for connecting the drip chamber to a source of fluid; illuminating, using the illumination system, a drop of the fluid hanging from the end of the drip tube; and using an optical system to: receive first light emanating from the end of the drip tube and second light emanating from the drop; and transmit data regarding the received first and second light to a specially programmed microprocessor. The method also includes using the microprocessor to: generate respective images of the end of the drip tube and the drop from the data; locate an apex of the drop, the apex being a portion of the drop at a furthest distance from the end of the drip tube; determine, using the location of the apex, an orientation of the drop with respect to the end of the drip tube; and calculate, using the orientation of the drop with respect to the end of the drip tube, an orientation of the drip chamber.

The invention broadly comprises a method for operating an infusion pump, including: transmitting light through a wall of a drip chamber for the infusion pump to a drop of fluid suspended from an end of a drip tube for the infusion pump, the drip tube being for connection to a source of fluid and the end of the drip tube being disposed in the drip chamber; controlling, using an illumination system for the infusion pump, illumination properties of the light transmitted to the drop; and using an optical system for the pump to: receive light transmitted through the drop; and transmit to a specially programmed microprocessor, data regarding the received light. The method also includes using the microprocessor to: generate, from the data, respective images of the drop and of the end of the drip tube; calculate, using the respective images, a boundary of the end of the drip tube; and calculate a volume, shape, or location of the drop using the boundary as a reference plane.

The invention broadly comprises a method for operating an infusion pump, including: transmitting light through a wall of a drip chamber for the infusion pump to an end of a drip tube or proximate the end of the drip tube, the drip tube being for connection to a source of fluid and the end of the drip tube being disposed in the drip chamber; controlling, using an illumination system for the infusion pump, illumination properties of the transmitted light transmitted to the drop; and using an optical system for the pump to: receive light transmitted through the end of the drip tube or proximate the end of the drip tube; and transmit, to a specially programmed microprocessor, data regarding the received light. The method also includes: using the microprocessor to: generate an image of the end of the drip tube from the data; determine, from the image, that a drop is absent from the end of the drip tube for a specified period of time; and generate an empty bag alarm or an air-in-line alarm.

The invention broadly comprises a method for operating an infusion pump, including: transmitting light through a wall of a drip chamber for the infusion pump to a drop of fluid suspended from an end of a drip tube for the infusion pump, the drip tube being for connection to a source of fluid and the end of the drip tube being disposed in the drip chamber; controlling, using an illumination system for the infusion pump, illumination properties of the light transmitted to the drop; and using an optical system for the pump to: receive light transmitted through the drop; and transmit, to a specially programmed microprocessor, data regarding the received light. The method also includes using the microprocessor to: create a plurality of temporally successive images of the drop from the data; calculate a respective volume for the drop in each successive image; identify changes in the respective volumes; and calculate a flow rate of fluid to the output tube based on the changes in the respective volumes.

The invention broadly comprises a method for operating an infusion pump, including: transmitting light through a wall of a drip chamber for the infusion pump to a drop of fluid suspended from an end of a drip tube for the infusion pump, the drip tube being for connection to a source of fluid and the end of the drip tube being disposed in the drip chamber; controlling, using an illumination system for the infusion pump, illumination properties of the light transmitted to the drop; and using an optical system for the pump to: receive light transmitted through the drop; and transmit, to a specially programmed microprocessor, data regarding the received light. The method also includes: displacing fluid from the drip chamber through the output tube by operating a pumping mechanism for the infusion pump acting on the output tube; and using the microprocessor to: create a plurality of temporally successive images of the drop from the data; calculate a respective volume for the drop in each successive image; identify changes in the respective volumes; calculate a flow rate of fluid to the output tube based on the changes in the respective volumes; and control the pumping mechanism to match the flow rate of fluid with a desired flow rate of fluid.

The invention broadly comprises a method of operating a dual infusion pump configuration, the configuration including a specially programmed microprocessor; first and second drip chambers connected to first and second output tubes, respectively; first and second drip tubes connected to first and second sources of fluids, respectively, and with first and second ends disposed in the first and second drip chambers, respectively; first and second illumination systems; and first and second optical systems, including: transmitting first and second light through walls of the first and second drip chambers to drops of the first and second fluids, suspended from the first and second ends of the first and second drip tubes, respectively; controlling, using the first and second illumination systems, first and second illumination properties of the first and second light transmitted to the drops of the first and second fluids, respectively; receiving, using the first and second optical systems, first and second light transmitted through the drop of the first and second fluids, respectively; transmitting, to the microprocessor and using the first and second optical systems, first and second data regarding the first and second received light; acting on the first and second output tubes, using the first and second pumping mechanisms, to displace first and second fluid from the first and second drip chambers through the first and second output tubes, respectively; and using the microprocessor to: operate the first pumping mechanism to generate a first flow rate for the first source of fluid from the first drip chamber through the first output tube; create, from the first data, a plurality of temporally successive images of the drop of the first fluid; determine, using the plurality of temporally successive images, that the first source of fluid is empty when the drop of the first fluid is absent from the first end of the first drip tube for a specified period of time; and operate the second pumping mechanism to generate a second flow rate for the second source of fluid from the second drip chamber through the second output tube in response to determining that the first source of fluid is empty.

BRIEF DESCRIPTION OF THE DRAWINGS

The nature and mode of operation of the present invention will now be more fully described in the following detailed description of the invention taken with the accompanying drawing figures, in which:

FIGS. 3A through 3F illustrate example embodiments of the illumination system shown in FIG. 2;

FIGS. 4A through 4C are schematic representation of embodiments for an optical system;

FIGS. 5A through 5C illustrate imaging processing definitions;

FIGS. 8A and 8B are schematic details for a pump implementing an operation for determining a gravity vector;

FIGS. 9A and 9B are schematic details of a pump using light injection;

FIGS. 10A and 10B are schematic details of a pump with a meniscus detection arrangement;

DETAILED DESCRIPTION

At the outset, it should be appreciated that like drawing numbers on different drawing views identify identical, or functionally similar, structural elements of the invention. While the present invention is described with respect to what is presently considered to be the preferred aspects, it is to be understood that the invention as claimed is not limited to the disclosed aspects.

Furthermore, it is understood that this invention is not limited to the particular methodology, materials and modifications described and as such may, of course, vary. It is also understood that the terminology used herein is for the purpose of describing particular aspects only, and is not intended to limit the scope of the present invention, which is limited only by the appended claims.

Unless defined otherwise, all technical and scientific terms used herein have the same meaning as commonly understood to one of ordinary skill in the art to which this invention belongs. Although any methods, devices or materials similar or equivalent to those described herein can be used in the practice or testing of the invention, the preferred methods, devices, and materials are now described.

Figure 1:
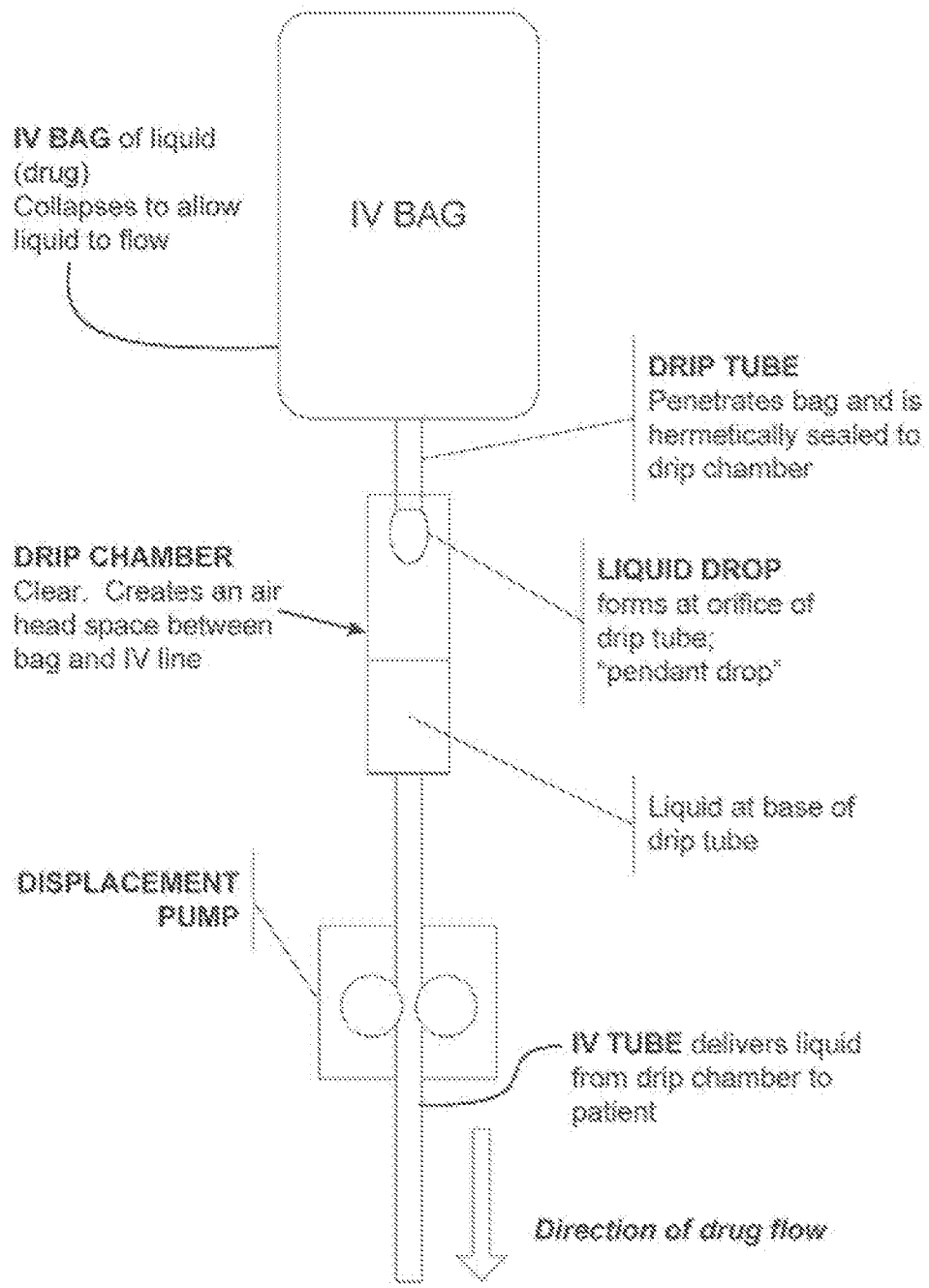
FIG. 1 is a schematic representation of definitions for an infusion pump.

FIG. 1 is a schematic representation of definitions for an infusion pump.

Figure 2:
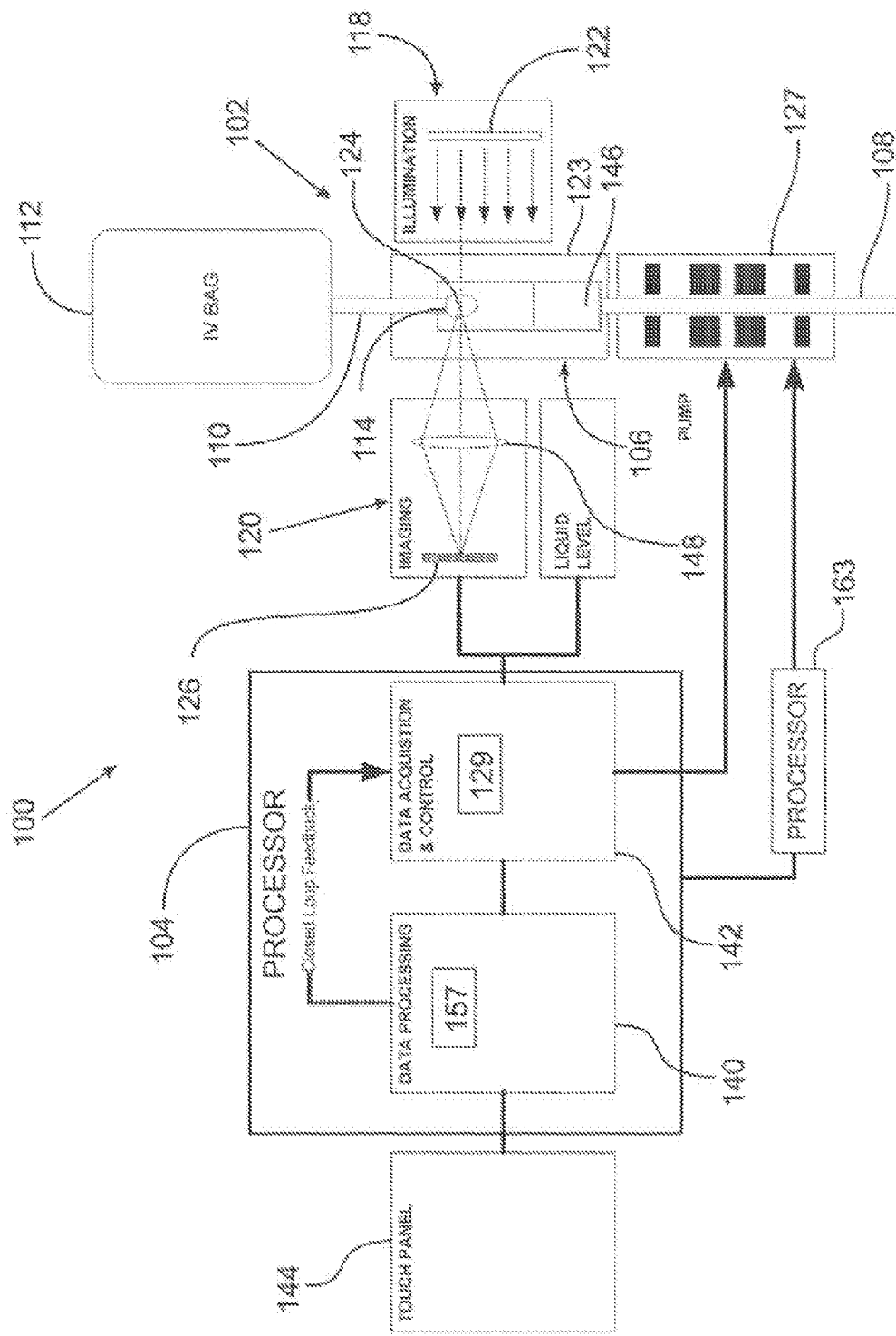
FIG. 2 is a schematic block representation of an infusion pump with an optical imaging system.

FIG. 2 is a schematic block representation of infusion pump 100 with optical imaging system 102. Pump 100 includes specially programmed microprocessor 104, drip chamber 106 for connection to output tube 108, and drip tube 110 for connecting the drip chamber to a source of fluid 112, for example, an IV bag. The drip tube includes end 114 disposed within the drip chamber. The imaging system includes illumination system 118 and optical system 120. System 118 includes lighting element 122 for transmitting light through wall 123 of the drip chamber to or around drop 124 of the fluid suspended from the end of the drip tube, for example, one or both of the drip and end 114 are illuminated. System 118 also controls illumination properties of the light transmitted to the drop. System 120 receives, for example using optical sensor 126, light transmitted through the drop, or through or around end 114 and transmits, to the microprocessor, data 129 regarding the received light. Pump 100 also includes pumping mechanism 127. In one embodiment, the mechanism includes top and bottom flow restrictors and uses peristaltic actuators, such as rollers, to displace fluid through tube 108.

Figure 3E:
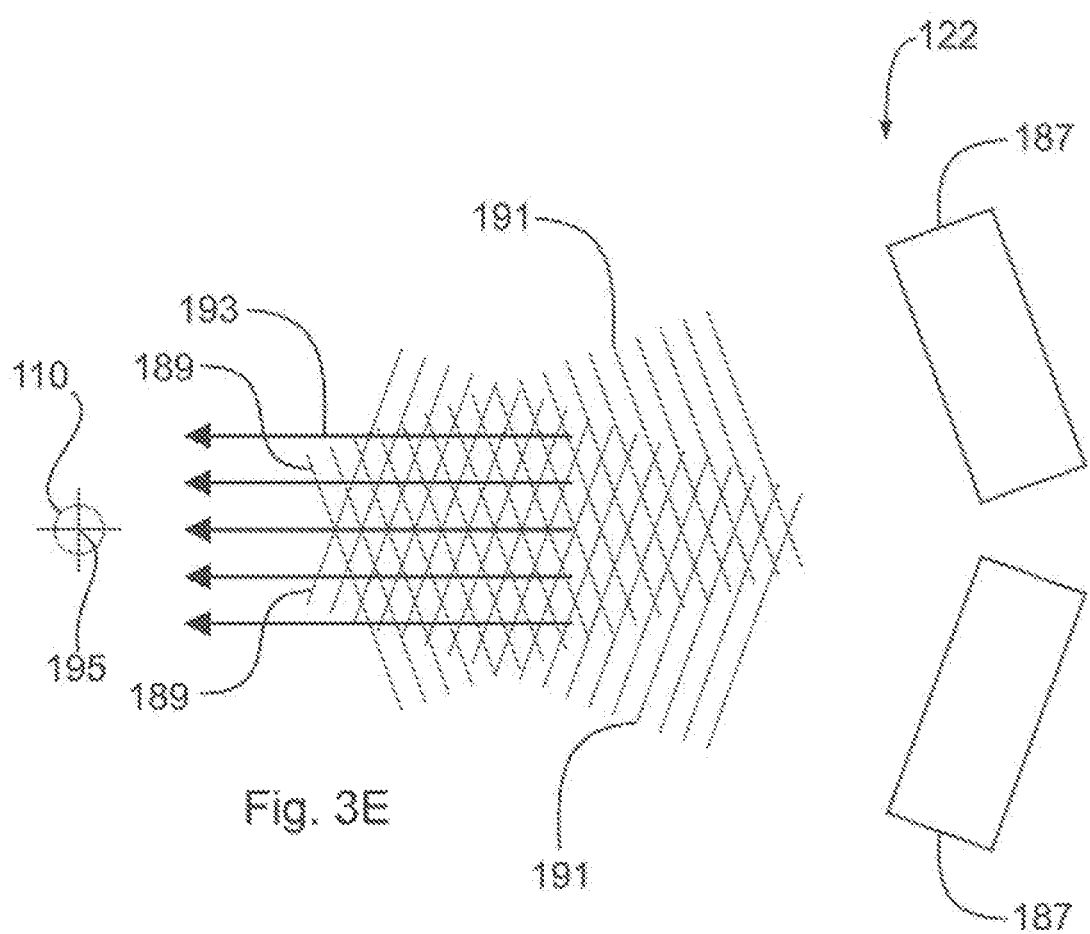

FIGS. 3A through 3F illustrate example embodiments of system 118 in FIG. 2. As shown in FIG. 3A, light rays 128 from a collimated illumination system are parallel. As shown in FIG. 3B, light rays 130 from a diffuse illumination system are emitted in a cone-shaped pattern from each light emitting point on an illumination plane. As shown in FIG. 3C, light rays 132 from illumination source 122 pass through telecentric lens 134 and are formed into ray bundles 136. The rays in bundles 136 are very nearly parallel. The ray bundles provide sharp definition of image edges and minimize depth distortion As shown in FIG. 3D, a structured lighting element shapes illumination, for example, rays 138, so as to control unwanted or stray light and to accentuate edges of an objecting being illuminated. A structured lighting element can include barrier 139, disposed between an illumination source and an object being illuminated, for example, drop 124, to shape the illumination, for example, by blocking or altering light emanating from the source.

FIG. 3E illustrates the use of laser interference to project stripe patterns measure drop 124. Illumination source 122 includes laser light sources 187. Sources 187 project light patterns consisting of many stripes at once, or of arbitrary fringes. This technique enables the acquisition of a multitude of samples regarding an image of drop 124, simultaneously. As seen from different viewpoints, the projected pattern appears geometrically distorted due to the surface shape of the object. In one embodiment, patterns of parallel stripes are used; however, it should be understood that other patterns can be used. The displacement of the stripes allows for an exact retrieval of the three dimensional (3D) coordinates of details on an object's surface, for example, the surface of drop 124. Laser interference works with two wide planar fronts 189 from laser beams 191. The interference of the fronts results in regular, equidistant line, or interference, patterns 193. Different pattern sizes can be obtained by changing the angle between the beams. The method allows for the exact and easy generation of very fine patterns with unlimited depth of field. FIG. 3E is a top view of pump 100 and sources 187 are shown disposed radially about axis 195 for drop tube 110. However, it should be understood that other configurations of sources 187 with respect to the pump are possible, for example, parallel to axis 195.

Figure 3F:
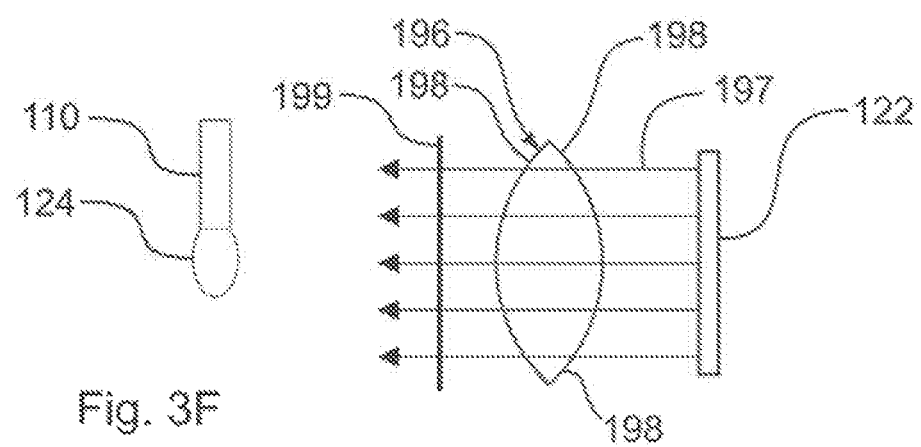

FIG. 3F illustrates the use of projection lens 196 in system 118. In FIG. 3F, system 118 illumination source transmits light 197 through lens 196. Surface 198 of the lens is modified as known in the art, for example, etched or through deposition of chrome or other materials, to produce a pattern on the surface. Light 197 passing through the lens projects an image of the pattern on and about drop 124. In one embodiment, projected pattern 199 is in the form of a constant-interval bar and space square wave, such as a Ronchi Ruling, or Ronchi grating.

The illumination source for a structured lighting element can be collimated, diffuse, or telecentric. Structured illumination can control unwanted or stray light and accentuate image edges. In one embodiment, the illumination system includes a telecentric lighting element. In one embodiment, the illumination system includes a structured lighting element.

Returning to FIG. 2, microprocessor 104 includes data processing segment 140 and data acquisition and control segment 142. The pump also includes control panel 144, for example, any graphical user interface known in the art. Output from the optical system, for example, data 129 from sensor 126, is inputted to segment 142. Panel 144, or other operator input, is used to input a desired flow rate through the drip chamber, as well as other necessary data such as drug type and treatment information. Microprocessor 104 can be any microprocessor known in the art.

Pump 100 uses optical sensing of pendant drops, that is drops hanging from or suspended from end 114, to measure fluid flow through the drip chamber to the output tube and to provide input to a closed-loop pump control process controlled by the microprocessor. Fluid from source 112 flows through drip tube to end 114 of the drip tube. The fluid forms drop 124 at end 114 and when conditions in the drip tube, discussed infra, are suitable, the drop falls from end 114 into fluid 146 in the drip chamber. In general, a pendant drop increases in size in proportion to the outflow of fluid 146 from the drip chamber through tube 108. That is, an increase in the volume of the pendant drop during a time frame is equal to the volume of fluid passing from the drip chamber to tube 108 in the time period. The preceding relationship is based on the following assumptions: the fluid from the source is not compressible; source 112, the drip tube, the drip chamber, tube 108, and a patient to whom tube 108 is connected are closed to outside atmosphere. Each measurement of the drop volume is processed to provide a fluid volume (or mass) measurement. Successive measurements of drop volume over known intervals of time are used by the microprocessor to calculate the flow rate of fluid through the system.

Thus, in one embodiment, operation of pumping mechanism 127 is controlled by the microprocessor using the desired set point for flow through the drip chamber and data regarding a measured flow rate of fluid through the drip chamber. For example, the microprocessor executes a feedback loop which compares the desired flow rate with the measured flow rate, and adjusts the pumping mechanism to correct any deviations between desired and measured flow rates.

FIGS. 4A through 4C are schematic representation of embodiments for optical system 120. The embodiments shown in FIGS. 4A through 4C form real, conjugate images, for example, of drop 124 on a focal plane array formed by sensor 126. FIGS. 4A and 4B use refractive optics, such as single lens 148 or combinations 150 of lenses, respectively. FIG. 4C shows refractive optics, such as combination 150 of lenses, and reflective optics, such as fold mirror 152. Lens 148, combination 150, and mirror 152 can be any lens, combination of lenses, or mirror known in the art. Combination 150 may include different lenses in FIGS. 4B and 4C.

Returning to FIG. 2, in one embodiment, optical sensor 126 is a focal plane array formed by any means known in the art, including, but not limited to a charge coupled device (CCD), a CMOS detector, or a hybrid imaging array such as InGaAs bonded to a CMOS readout integrated circuit. System 120 includes optics, such as lens 148, focused on the location of drop 124. It should be understood that other optics can be used in system 120. In one embodiment, chamber 106 is substantially optically clear and system 118 directs light though the walls of the chamber to the optical system, for example, sensor 126. The light can provide back or side illumination of the drop. In one embodiment, system 102 is configured such that drop 124 and the focal plane array are optical conjugates and the focal plane array records an actual image of the drop. The imaging system captures drop images at a rate sufficient to observe the growth and detachment of a single drop.

In one embodiment, pump 100 satisfies two key metrics with respect to imaging drop 124. First, the frame rate (images per second) is sufficient to capture a sequence of images as the drop grows in size and detaches. Second, the exposure time (the amount of time the light is collected on the sensor for each specific image) is short enough to freeze the motion of the drop. Pump 100 generates images with clear edge definition, sufficient magnification (in terms of number of pixels across the drop), and a minimum number of artifacts such as glare.

In one embodiment, imaging system 102 and the microprocessor produce an accurate image of the drop that is then analyzed as described infra to determine the volume of the drop. Since the fluid drop has a uniform density, and any bubbles (occlusions) or entrainments are sufficiently small to be negligible, in one embodiment, only the outer surface of the drop is measured to calculate the volume of the drop. The preceding measurement is accomplished by imaging the drop with sufficient spatial resolution to accurately measure the boundary surface. A numeric integral over this boundary then provides the droplet volume.

FIGS. 5A through 5C illustrate imaging processing definitions. In one embodiment, a reference/alignment frame and an image scale (pixels per mm) are established by locating end point 114 of the drip tube orifice, as shown in FIG. 5A. The end point has a known size and hence provides scale calibration. The end point also represents the top boundary of the drop, which is used in volume calculations described infra. In one embodiment, apex 154 of the drop (a point furthest from the fixed/reference point) is identified and used in the determination of the volume of the drop. For example, the optical system, for example, sensor 126, receives the light transmitted into or through the drip tube and transmitting, to the microprocessor, data regarding the received light. In one embodiment, the microprocessor is for determining, using the data, a boundary of end point 114 and using the boundary of end point 114 as a reference point for determining a volume, shape, or location of the drop, as further described infra.

In one embodiment, as further described infra, the direction of gravity (gravity vector 156) with respect to drop 124 is determined. A reference point, for example, the boundary of end point 114, and the gravity vector are used to establish a reference frame for the image processing.

In one embodiment, volume of drop 124 is calculated by using the microprocessor to receive data 129 and generate an image of the drop from the data. The microprocessor locates an outer edge of the drop in the image to define boundary 157 of the drop. The microprocessor integrates an area enclosed by the boundary and calculates a volume of revolution for the drop with respect to axis 159 for the drop that intersects the end of the drip tube, assuming symmetry of the drop with respect to the axis.

The above calculation of the volume of drop 124 can be calculated using at least two broad approaches. The first approach, termed Boundary Constrained Volume and shown in FIG. 5B, uses the outer location of the drop image to calculate the total volume. Each horizontal row 158 of pixel data from the image has associated with it an outer left and right boundary. The area between these boundaries is treated as the two dimensional projection of a circular disk volume (the symmetric volume of rotation of the area). The drop image is integrated from end point 114 to the apex by summing the volume of each row. Boundary Constrained Volume obtains maximum resolution for each row of data.

The second approach is termed Fit Constrained Volume and is shown in FIG. 5C. That is, the volume of drop 124 is determined by fitting a parametric function to the boundary image of the drop and integrating the parametric function, again, assuming rotational symmetry. There are a number of possible fitting algorithms, as discussed below, but the result of any fit is a set of parameters to the assumed function that represents entire boundary 157. Fit Constrained Volume smoothes out row detail.

In one embodiment, the microprocessor creates a plurality of temporally successive images of the drop from data 129 and calculates a respective volume for the drop in each successive image or calculates respective time periods between detachment of successive drops from the end of the drip tube. By temporally successive images, we mean a series of images taken over a time period in chronological order. The microprocessor calculates a rate of increase for the volume of the drop using the respective volumes or the respective time periods. As noted above, flow out of the drip tube is substantially equal to the increase in the volume of the drop; therefore, the time periods between drops detaching from the end of the drip tube can be correlated to the volume increases of the successive drops. For example, in one embodiment, the microprocessor calculates a respective volume for the drop in each successive image, for example, using operations described infra and supra; calculates changes in the respective volumes; and calculates a flow rate of fluid to the output tube based on the changes in the respective volumes. In one embodiment, the microprocessor controls mechanism 127 to match the calculated flow rate with a desired flow rate, for example, stored in the microprocessor.

In one embodiment, the microprocessor is for generating a free flow alarm or an out of bound condition alarm when the rate of increase for the volume of the drops exceeds a predetermined value, for example, stored in the microprocessor. In one embodiment, the microprocessor is for operating mechanism 127 to shut off flow to the output tube when the free flow alarm or the out of bound condition alarm is generated. In one embodiment the microprocessor generates a downstream occlusion alarm when the rate of increase of the volume of the drop is less than a predetermined value. In one embodiment, the microprocessor determines that a drop is absent from the end of the drip tube for a specified period of time and generates an empty bag alarm or an air-in-line alarm.

In one embodiment, the pump includes processor 163 used to operate mechanism 127 to shut off flow to the output tube when the free flow alarm or the out of bound condition alarm is generated. That is, as a safety and redundancy factor, a second microprocessor is used in the pump.

The drop is initially hanging from a fixed point in the drip chamber, for example, end 114. In one embodiment, the microprocessor is for identifying when the drop detaches from the fixed point in the drip chamber as a means of determining when the drop has reached maximum volume. The microprocessor makes the preceding identification by creating a plurality of temporally successive images of the drop and analyzing these images. By temporally successive images, we mean a series of images taken over a time period in chronological order.

In one embodiment, the microprocessor identifies, in each successive image, a respective point in the boundary, for example, apex 154, and determines a distance of each respective point from end 114. The microprocessor then identifies two successive images of the drop in which the distance, noted above, in the second image in the succession is less than the distance in the first image in the succession. This decrease of the distance indicates that the drop detached from the fixed point in the interval between the first and second images, which further indicates that the drop reached a maximum size in the first image. The microprocessor calculates the volume of the drop using the first image.

Figure 6:
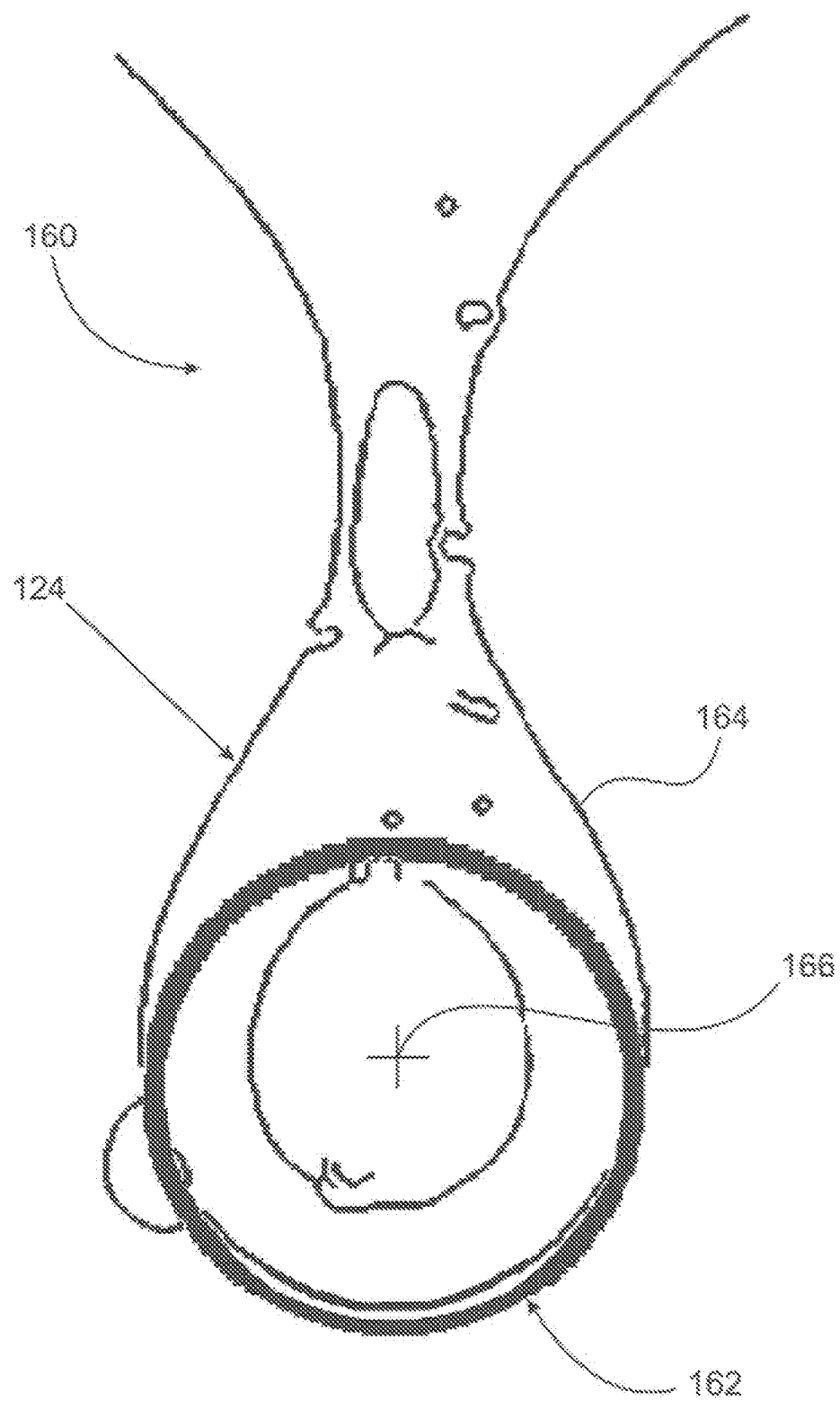
FIG. 6 illustrates an image of a drop including a circle at least partly included within an outer boundary of the drop

FIG. 6 illustrates image 160 of drop 124 including circle 162 at least partly included within outer boundary 164 of the drop. FIG. 6 illustrates a specific example of the Fit Constrained Volume approach. In one embodiment, the microprocessor identifies respective circles 162 within each temporally successive image. The circles are partially defined by a respective outer boundaries 164 of the temporally successive images. The microprocessor identifies a respective location, with respect to the fixed point in the drip chamber, for each respective circle and calculates a volume of the drop from the data and using the respective circles.

In one embodiment, identifying the respective location for said each respective circle includes identifying the image corresponding to the largest size of the drop, for example, the last image before the drop detaches from the end point of the drip tube. For example, the microprocessor identifies a respective point on each respective circle at a furthest distance from the fixed point in the drip chamber, for example, end point 114. The microprocessor then determines which of the respective points is furthest from the fixed point and identifies an image including the respective point furthest from the fixed point. That is, the microprocessor identifies the largest drop by identifying the drop having the largest circle. In one embodiment, the largest drop is identified by determining a first image in which the distance of the apex from the fixed point decreases with respect to the distance of the apex from the fixed point for a second image immediately preceding the first image. This decrease indicates that the drop detached from the fixed point in the interval between the first and second images, which further indicates that the drop reached a maximum size in the first image. The microprocessor calculates the volume of the drop using the image including the respective point furthest from the fixed point.

In one embodiment, the microprocessor identifies the respective outer boundaries for each of the temporal images such that each outer boundary includes a respective edge of the drop furthest from the fixed point in the drip chamber and the respective circle includes the respective edge. That is, the microprocessor aligns the circles described supra with the actual edges of the drops such that the points of the circles furthest from the fixed point, for example, end 114, are part of the edge of the drop. In one embodiment, the microprocessor identifies respective circular arcs corresponding to the respective edges and including the respective circular arcs in the respective circles.

In one embodiment, identifying the image corresponding to the largest size of the drop, for example, the last image before the drop detaches from the end point of the drip tube, includes using the center points of the circles. For example, the microprocessor calculates respective center points 166 for the circles and calculates the positions of the center points with respect to the fixed point, for example, end point 114. The microprocessor then determines which of the center points is furthest from the fixed point and identifies an image including the center point furthest from the fixed point. That is, the microprocessor identifies the largest drop by identifying the drop having the largest circle. The microprocessor calculates the volume of the drop using the image including the center point furthest from the fixed point.

Figure 7:
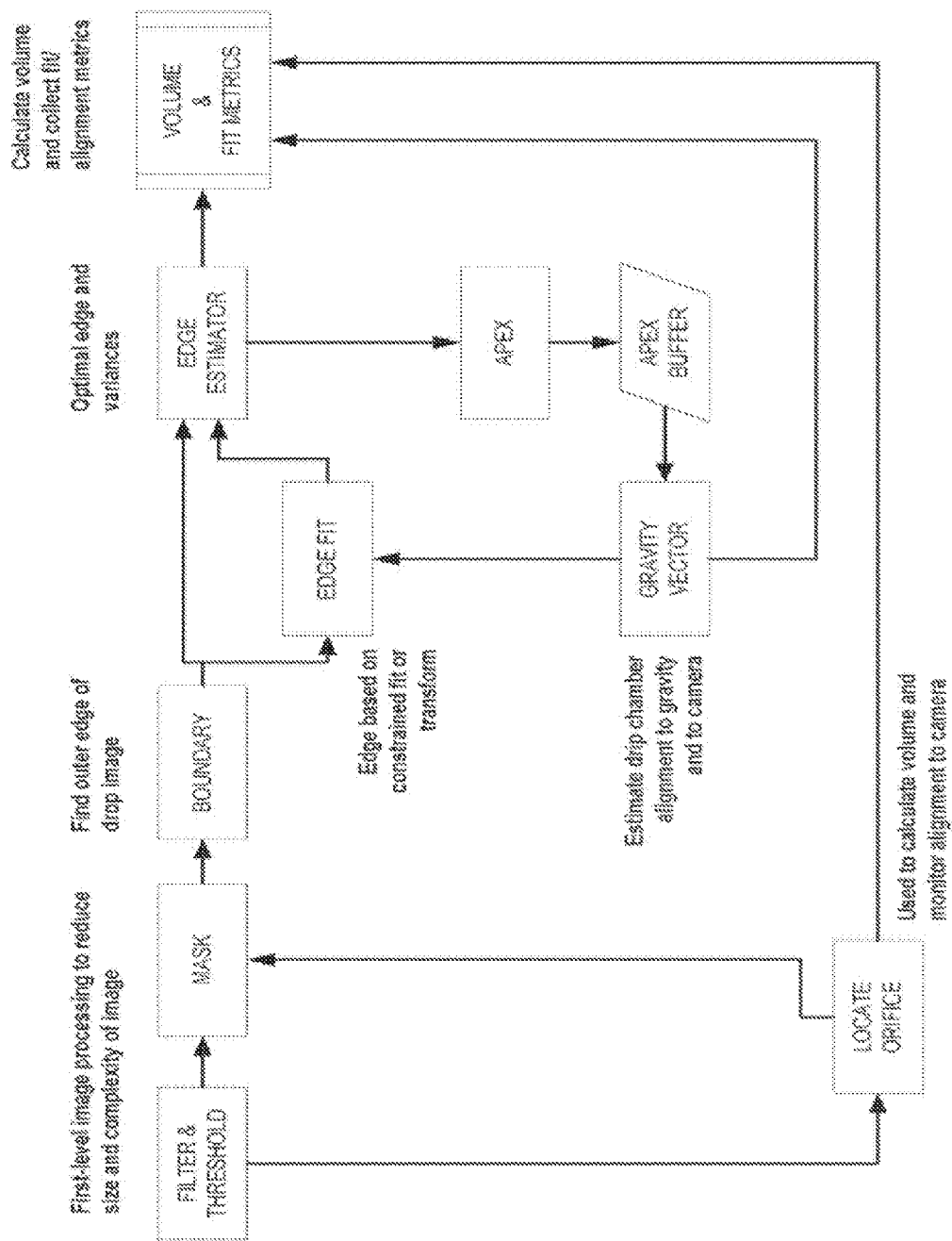
FIG. 7 is a flow chart illustrating operation of a pump with an optical imaging system.

FIG. 7 is a flow chart illustrating operation of pump 100 with an optical imaging system. FIG. 7 illustrates an example algorithm usable by pump 100. It should be understood that other algorithms are usable by the pump. The image of drop 124 is filtered and thresholded to create a binary image. Filter operations can include median filtering (to remove isolated glare), background and image uniformity correction (to remove noise sources due to dark noise, read noise, pixel non-uniformity, and illumination non-uniformity), and edge definition (using techniques such as convolution or unsharp masking). The resulting images are thresholded to yield binary images. A binary image consists of values that are either black or white, with no intermediate gray scale values. The images are also processed (in parallel with the above operations) to find the reference location, for example, end point 114, using techniques such as feature detection, pattern matching, or transform techniques such as the Radon transform. The end point location is used to form an image mask. A mask isolates a region of an image for further processing. Use of a mask increases computational speed, as well as eliminates artifact information from being further processed.

In one embodiment, the binarized, masked images are then processed row-by-row to find the extreme right- and left-boundaries. This boundary-constrained fit is one estimate of the drop edge shape. In one embodiment, the images are also processed using a fit-constrained algorithm. Such an algorithm applies constraints based on assumptions about the drop shape as discussed supra and infra. The constraints are used in a non-linear least squares optimization scheme to minimize the error between the parameterized constraint function(s) and the set of binarized edge images.

The two different edge approximations are provided to an Edge Estimator algorithm that compares fit-constrained images to boundary-constrained images. In the simplest instantiation, the images are compared row-by-row. The boundary-constrained images are considered to be the "correct" result unless they deviates from the fit-constrained images by more than a certain parameter (this parameter is adjusted during calibration). If the deviation is too large, the value from the fit-constrained image is used to replace that of the boundary-constrained image for that row. The above is intended to illustrate the concept behind the estimator. In actual use, more sophisticated algorithms are used to simultaneously optimize the difference between the two initial estimates. An example of such an algorithm is a Kalman filter, but other algorithms familiar to those skilled in the art may also be utilized.

The output from the Edge Estimator also provides the location of the apex of the drop, which is for example, used to calculate the time-dependent gravity vector. This operation requires access to prior estimates of the apex value (to calculate the change), and hence a number of prior values are stored in a buffer. The gravity vector is required for some of the parametric fit functions that are used in the fit-constrained edge estimation algorithms. Hence, the gravity vector is used in a feedback loop for the edge fit algorithms.

FIGS. 8A and 8B are schematic details for pump 100 implementing an operation for determining gravity vector 156. In one embodiment, system 118 illuminates end point 114 and drop 124 and the optical system, for example, sensor 126, receives light emanating from the end point and light emanating from the drop and transmits data 129 regarding the received light. The microprocessor generates, using the data, respective images of the drop and the end of the drip tube and locates an apex of the drop, the apex being a portion of the drop at a furthest distance from the end of the drip tube. The microprocessor determines, using the location of the apex, an orientation of the drop with respect to the end of the drip tube and calculates, using the orientation of the drop with respect to the end of the drip tube, an orientation of the drip chamber. In one embodiment, the microprocessor compares the orientation of the drip chamber to a set point, for example, a certain orientation with respect to plumb stored in the microprocessor, and generates an out of bound condition alarm when the orientation equals the set point or varies from the set point by a specified amount. For example, if the drip chamber is too far out of plumb, operation of pump 100 may be compromised and the alarm is generated.

For example, in FIG. 8A line 168 for the actual orientation of the drop and axis 170 for the drip chamber are co-linear, Since the drop must necessarily align with the forces of gravity (is plumb), the drip chamber is in a plumb orientation in FIG. 8A. Also, line 168 is aligned with gravity vector 156. In FIG. 8B, lines 168 and 170 are not co-linear and the drip chamber is not plumb. Thus, in one embodiment, the microprocessor generates lines 168 and 170 and compares the respective locations or orientation of the lines. That is, the microprocessor calculates the orientation of the drip chamber with respect to the gravity vector. In one embodiment, when data 129 is used to generate respective images over a period of time (temporally sequential images), the gravity vector is determined by measuring in the images of the end of the drip tube and the drop, the location of the apex of the pendant drop as it grows over time and tracking the time-dependent directional change of the apexes over a series of these measurements. In one embodiment, the boundary of end 114 is calculated as described supra and the boundary is used as reference plane for calculating the orientation of the drop and/or the drip chamber.

In one embodiment, the illumination system controls illumination properties of the light illuminating the end of the drip tube and the drop and the microprocessor: identifies respective boundaries of the end of the drip tube and the drop from the respective images; fits a parametric function to the respective boundaries; and integrating the parametric function to obtain a volume of the drop, for example, as described above.

In one embodiment, the end point location, gravity vector, and optimal edge estimate are input to a volume calculation routine that integrates the edge image using the "circular disk" assumption discussed above. The location of the end of the drip tube is used to determine the upper limit of integration, while the gravity vector is used to determine the direction of the horizontal (at right angles to the gravity vector). These end and gravity data values are provided along with the volume as output from the algorithm. In one embodiment, the algorithm also passes out the parameters of the edge fit, as well as statistical data such as fit variances. In one embodiment, the preceding information is used in the digital signal processing chain discussed below.

A number of methods can be used to fit a constraint to the measured image. In one embodiment, a "pendant drop" approach, involves solving the Laplace-Young equation (LYE) for surface tension. A drop hanging from a contact point (the end point) has a shape that is controlled by the balance of surface tension (related to viscosity) and gravity. The assumption is only strictly valid when the drop is in equilibrium; oscillations (due to vibration or pressure fluctuations) will distort the drop shape from the Laplace-Young prediction. However, small oscillations will not cause the fit to fail; in fact, the deviation from a fit is itself a good indicator of the presence of such oscillations.

In one embodiment, a Circular Hough Transform (CHT) is used on the image to identify the component of the image that represents the curved bottom of the drop. While not strictly a "fit", the CHT provides a parametric representation of the drop that is characterized by the value and origin of the radius of a circle. The CHT algorithm is representative of a constraint that is determined or applied in a mathematical transform space of the image. Other widely-used transforms, familiar to those skilled in the art, are the Fourier and wavelet transforms, as well as the Radon transform.

The parametric fitting procedures described above apply strong constraints on the possible location of the edge of the drop. Along with the assumption of continuity (a fluid edge cannot deviate from its neighbors over sufficiently short distances), and the requirement that the drop edge terminate at the drip tube orifice, the procedures are used to augment and correct the boundary-constrained image, as discussed above. Other fitting procedures work similarly to those discussed herein.

FIGS. 9A and 9B are schematic details of pump 100 using light injection. Drip tube 110, drip chamber 106, tube 108, drop 124, imaging system 120, and sensor 126 are as described for FIG. 2. Illumination system 118 includes illumination source 172 for transmitting, or injecting, light 174 into the drip tube. The light reflects off a plurality of portions of internally facing surface 176 of the drip tube and the reflected light is transmitted through the end point 114 of the drip tube into interior 177 of drop 124 such that the interior is uniformly illuminated. The optical system receives light 178 transmitted from the interior of the drop and transmits, to the computer processor, data regarding the received light. The data regarding the received light can be operated upon using any of the operations noted supra. For example, in one embodiment, the illumination system is for controlling illumination properties of the light transmitted to the drop, and the optical system is for receiving light from the drop. The microprocessor is for: generating an image from the data, the image including a boundary of the drop; fitting a parametric function to the boundary of the drop; and integrating the parametric function to obtain a volume of the drop.

Thus, light 174 is formed into a beam, which is injected into the transparent drip tube so as to undergo significant internal reflection (i.e., equal to or greater than the so-called "critical angle"). The cylindrical bore of the tube causes the internal reflections to diverge inside the tube (filling the bore of the tube), while imperfections in the tube surface introduce light scattering. The result is that the drop is illuminated internally. Under these conditions the imaging optics in system 120 receive only light that is scattered from the drop surface (there is no direct ray path for the light to reach the lens). In addition to a high contrast edge image, this approach enables the use of a very compact illumination element.

FIG. 10A is a schematic detail of pump 100 with a meniscus detection arrangement. Drip tube 110, drip chamber 106, tube 108, and fluid 146 are as described for FIG. 2. Imaging system 102 includes light source, for example, a laser, for transmitting light 182 at an acute angle with respect to longitudinal axis 184 for the drip chamber, into the drip chamber such that the light reflects, at the acute angle, off a surface 186 of fluid pooled within the drip chamber. System 102 also includes sensor, or position sensitive detector, 188 for receiving reflected light 182 and transmitting, to the computer processor, data regarding the received light. The microprocessor is for calculating a position of surface 186 using the data regarding the received light.

The location on sensor 188 receiving light 182 depends on the location of surface 186. Levels 190A and 190B show two possible levels for fluid 146 and hence, two possible locations for surface 186. As seen in FIG. 10B, light 182A and 182B reflecting from levels 190A and 190B, respectively, strike different portions of sensor 188. The microprocessor uses the difference between the locations on sensor 188 to determine the level of fluid 146, that is, the meniscus, in the drip chamber. Sensor 188 can be any positional sensitive detector known in the art, for example, a segmented sensor or a lateral sensor. In one embodiment, the microprocessor generates an empty bag alarm or an air-in-line alarm for an instance in which the light transmitted from light source 188 is not received by the optical system, for example, the drip chamber is empty or level 186 is so low that light 182 does not strike fluid 146.

A segmented positional sensitive detector includes multiple active areas, for example, four active areas, or quadrants, separated by a small gap or dead region. When a symmetrical light spot is equally incident on all of the quadrant, the device generates four equal currents and the spot is said to be located on the device's electrical center. As the spot translates across the active area, the current output for each segment can be used to calculate the position of the spot. A lateral positional sensitive detector includes a single active element in which the photodiode surface resistance is used to determine position. Accurate position information is obtained independent of the light spot intensity profile, symmetry or size. The device response is uniform across the detector aperture, with no dead space.

FIG. 10B is a schematic detail of pump 100 with a meniscus detection arrangement. In one embodiment, imaging system 102 includes mirror 192 on the opposite side of the drip tube to reflect light 182 back through the drip tube and beam splitter 194 to direct the reflected light to sensor 188. This configuration enables placement of all the electronics for the optical components on the same side of the tube.

The following provides further detail regarding meniscus level measurement. The drip chamber remains partially filled with fluid at all times during operation. The air trapped in the drip chamber is in pressure equilibrium with the fluid above and below it. The difference in pressure across the air gap drives fluid out of the bottom of the drip chamber and through downstream tubing 108. Fluid enters and leaves the drip tube chamber continuously as the drop grows in volume, and hence the meniscus level of the fluid remains nearly constant. However, changes in the meniscus level can occur for several reasons: transient changes may occur when a drop detaches and falls into the fluid below; or fluctuations may occur due to pressure oscillations in the fluid (due to pump vibration, motion of the tubing set, or motion of the patient). These transient changes will fluctuate around a mean meniscus value, and hence do not indicate changes in flow rate over times long compared to the characteristic fluctuation times.

Variations that change the mean meniscus level over longer times may occur due to changes in the external pressure environment (e.g., in a traveling vehicle or aircraft), changes in backpressure arising from medical issues with the patient, or due to occlusions or other malfunctions in the pumping process. These long-term meniscus level changes represent a concomitant change in the overall flow rate, and may be used to provide a refinement to the flow measurements described supra. Hence, it may be desired to monitor the level of the meniscus during the infusion, and to use the information derived therein as an indicator of operational problems with the infusion system, or as an adjunct to the primary optical flow measurement.

The method described above for measuring the level of fluid 146 uses the reflection of a light beam from the top surface of the fluid in the drip chamber. The axis of the reflected beam is shifted (deflected) laterally as the fluid level changes, for example, as shown by light 182A and 182B. The amount of deflection depends only on the fluid level change, and on the incident angle of the beam. Although a laser light source is shown in the figure, the technique is compatible with any light beam. Further, although the beam is shown freely propagating, the system may also incorporate lens elements to control the beam.

In one embodiment (not shown), sensor 126 (the imaging focal plane array) is used both for imaging drop 124 and measuring the meniscus of fluid 146 via beam splitters and other simple optics. Sensor 126 can be shared in at least two ways: a portion of the sensor that is not used for pendant drop imaging can simultaneously record the deflected beam; or illumination system 118 for pendant drop imaging and meniscus level measurement can be alternated in time, such that the sensor alternately records the drop image and the deflected beam image. For example, pump 100 can combine the imaging systems 102 shown in FIGS. 2 and 10A/10B or shown in FIGS. 2 and 9A.

Thus, in one embodiment, system 102 includes a first light source, such as light source 172 for transmitting light into the drip tube such that the light reflects off an internally facing surface of the drip tube, and the reflected light is transmitted through the end of the drip tube into an interior of a drop of the IV fluid hanging from the first end of the drip tube. System 102 also includes a second light source, such as light source 188, transmitting light, at an acute angle with respect to a longitudinal axis for the drip chamber, into the drip chamber such that the light reflects, at the acute angle, off a surface for IV fluid disposed within the drip chamber. Optical sensor 126 is for: receiving the reflected light transmitted from the interior of the drop; receiving the reflected light from the second light source; and transmitting, to the computer processor, data regarding the received light from the first and second light sources. The microprocessor is for calculating a volume of the drop using the data regarding the light received from the first light source, and calculating a position of the surface of the using the data regarding the light received from the second light source, as described supra.

Figure 11:
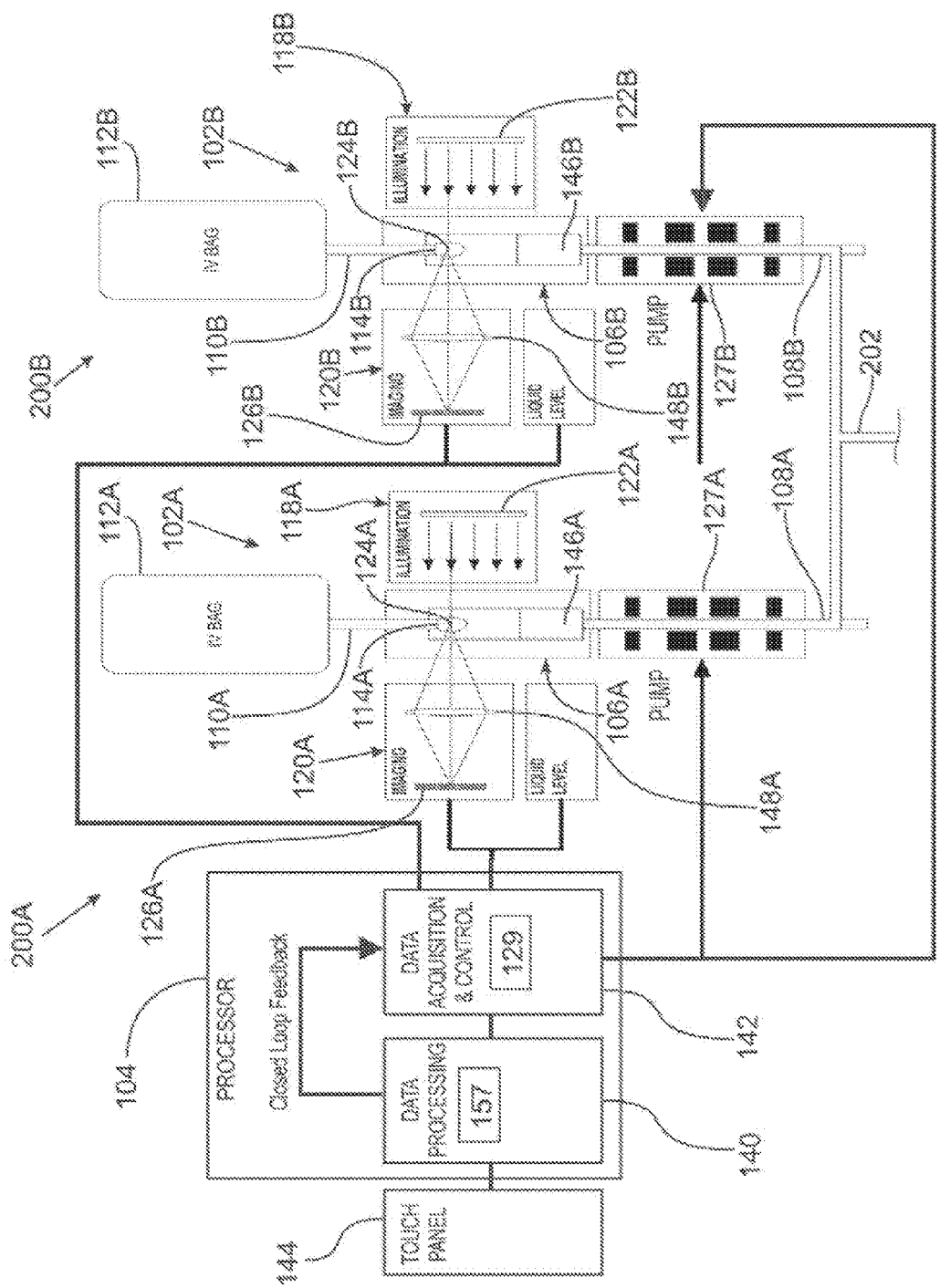
FIG. 11 is a schematic block representation of two infusion pumps with respective optical imaging system in a primary and secondary configuration.

FIG. 11 is a schematic block representation of pump assemblies 200A and 200B with respective optical imaging system in a primary and secondary configuration. The assemblies include the components for pump 100 described supra, with the exception of the processor and control panel. In general, the description above regarding the operation of pump 100 is applicable to the operation of assemblies 200A and 200B. Assembly 200A is connected to primary fluid source 112A. Pump 200B is connected to primary fluid source 112B. Sources 112A and 112B are arranged in a primary/secondary infusion configuration. For example, a primary medication in source 112A is administrated in coordination with a secondary medication in source 112B. As is known in the art, in a primary/secondary configuration, the medication in the secondary source is infused before the medication in the primary source. Tubings 108A and 108B from pump mechanisms 127A and 127B, respectively, are connected to common tubing 202.

In one embodiment, a single processor and control panel, for example, processor 104 and panel 144 are used for assemblies 200A and 200B. The processor operates assembly 200B according to appropriate protocols until the regime for the fluid in source 112B is completed. Then, the processor automatically deactivates assembly 200B as required and begins the infusion of the fluid in source 112A. In one embodiment (not shown), each assembly has a separate processor and control panel or each assembly has a separate processor and a common control panel.

Figure 12:
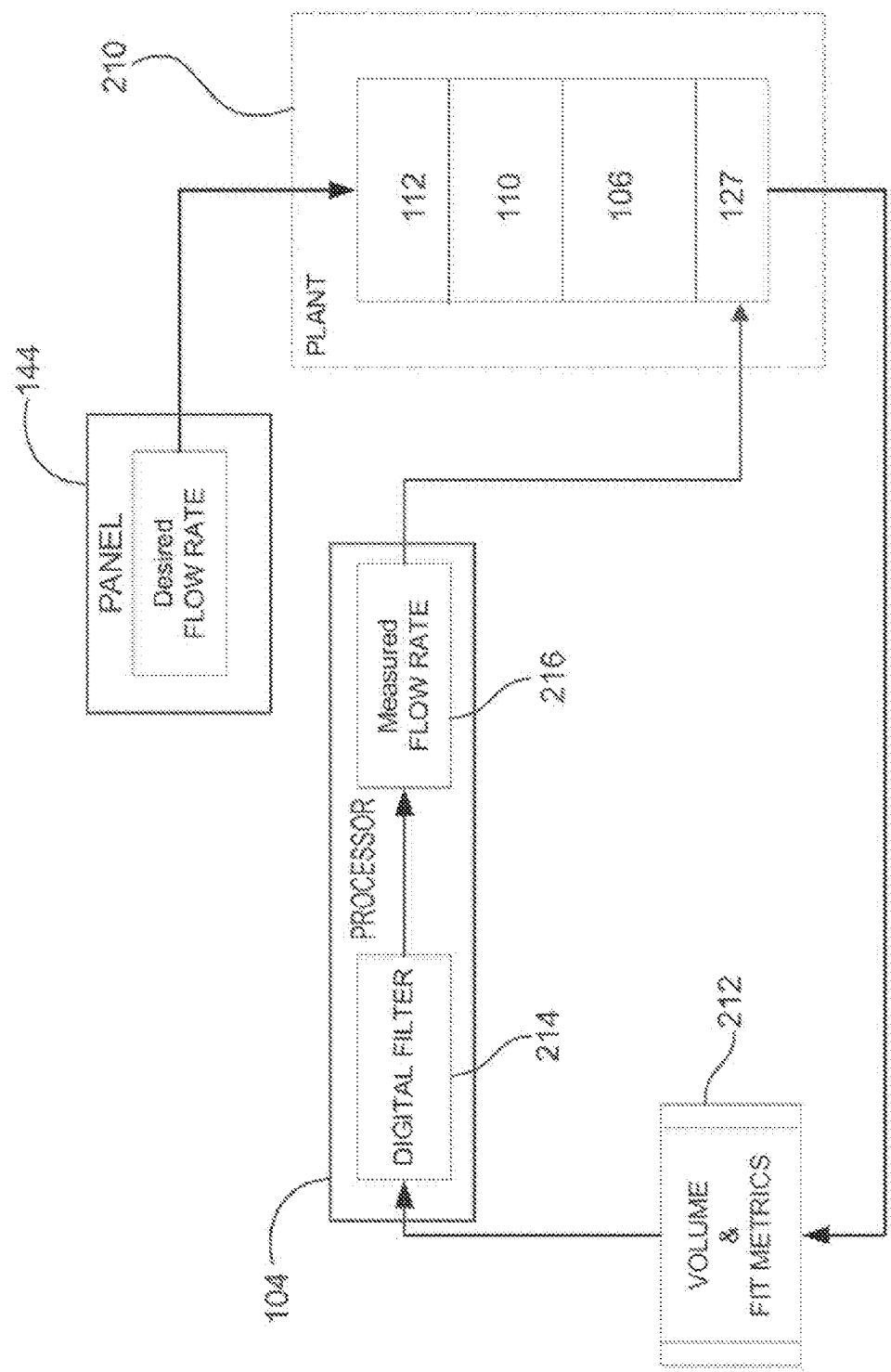
FIG. 12 is a top-level block diagram illustrating operation of a pump with an optical imaging system.

FIG. 12 is a top-level block diagram illustrating operation of pump 100 with an optical imaging system. In one embodiment, the volume measurement, and fit metrics if applicable, described above are fed into a digital signal processing algorithm that calculates the flow rate and provides feedback to the pump control system. Plant 210 includes source 112, the drip chamber, the drip tube, and pump mechanism 127. The microprocessor outputs the Volume and Fit Metrics 212, which are filtered by digital filter 214 in a portion of the microprocessor to provide measured flow rate 216. The measured flow rate is compared with the desired flow rate, for example, input into the microprocessor via panel 144, closing the feedback loop for pump 100.

Figure 13:
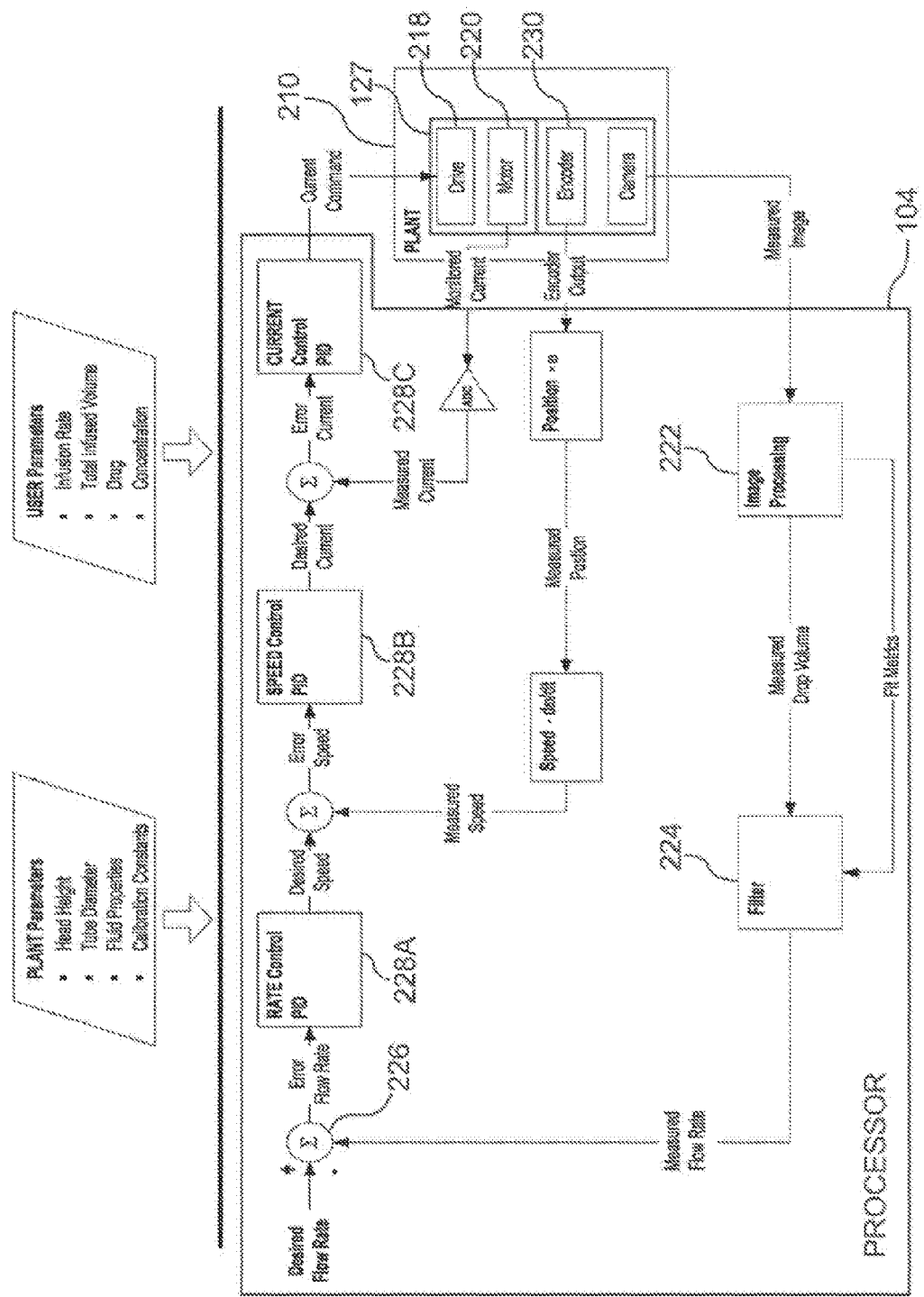
FIG. 13 is a block diagram illustrating example signal processing and feedback control for a pump with an optical imaging system.

FIG. 13 is a block diagram illustrating example signal processing and feedback control for pump 100 with an optical imaging system. Mechanism 127 includes drive 218 and motor 220. Imaging data from system 102 is processed by image processing block 222 to generate a Measured Drop Volume, and the results are input to filter block 224. The output of the filter block is the Measured Flow Rate. The Measured Flow Rate is compared to the Desired Flow Rate by comparator 226, providing the Error Flow Rate (error estimate). The Error Flow Rate feeds into a staged series of PID (Proportional, Integral, Derivative) control algorithms 228. Each PID block operates on a successively faster time scale. Block 228A controls the flow rate, block 228B controls the pump motor speed, and block 228C controls the pump motor current. The speed control incorporates feedback from motor position encoder 230. The current control incorporates feedback from a motor current sensor in motor 220.

Figure 14:
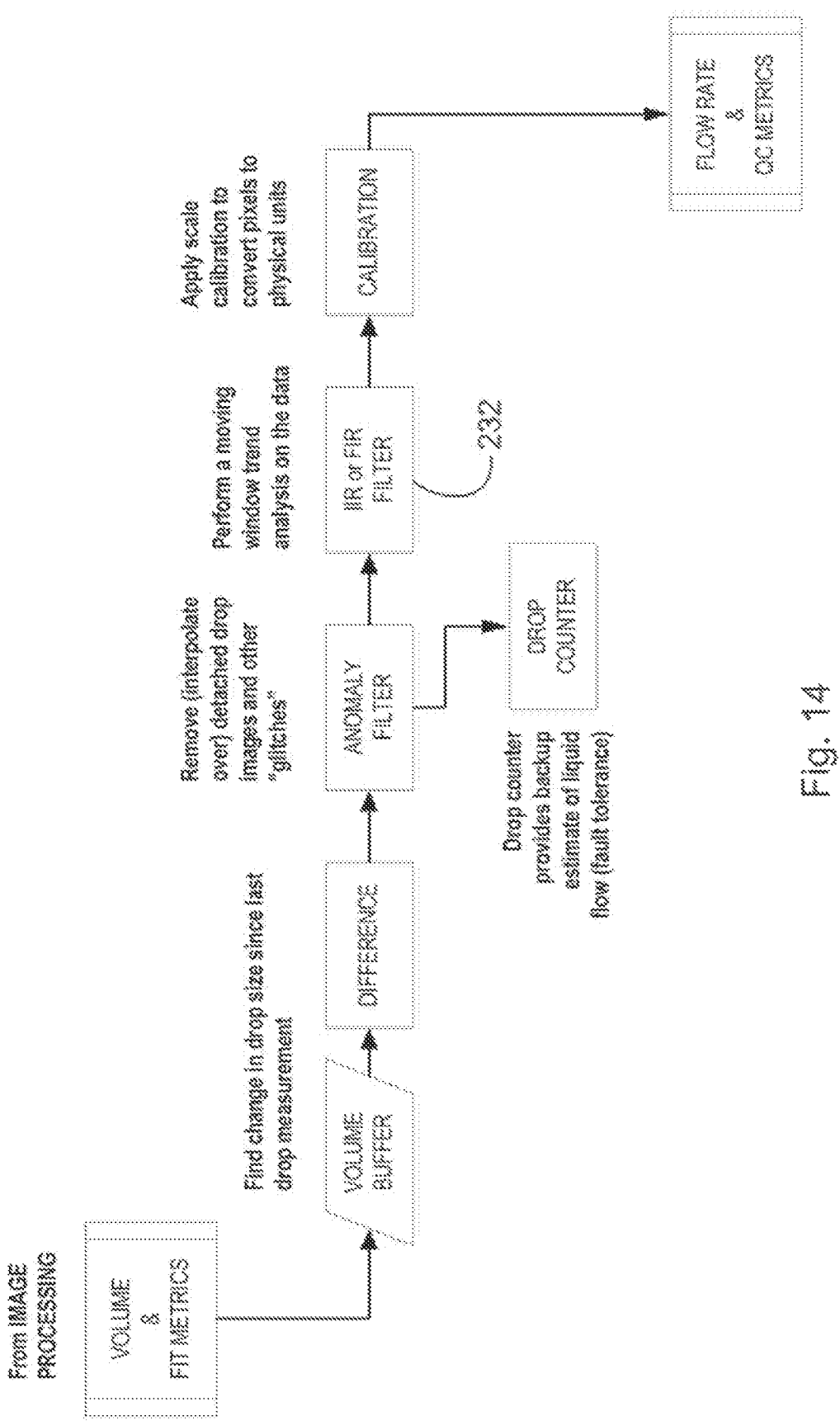
FIG. 14 is a block diagram illustrating example digital filtering in a pump with an optical imaging system; and, FIG. 15 is a schematic representation of example spatial filtering in a pump with an optical imaging system.

FIG. 14 is a block diagram illustrating example digital filtering in pump 100 with an optical imaging system. Filter 232 can be any filter known in the art, for example, the general class of FIR/IIR filters known to those skilled in the art. A simple example is an FIR filter that implements a time average over a number of samples.

Figure 15:
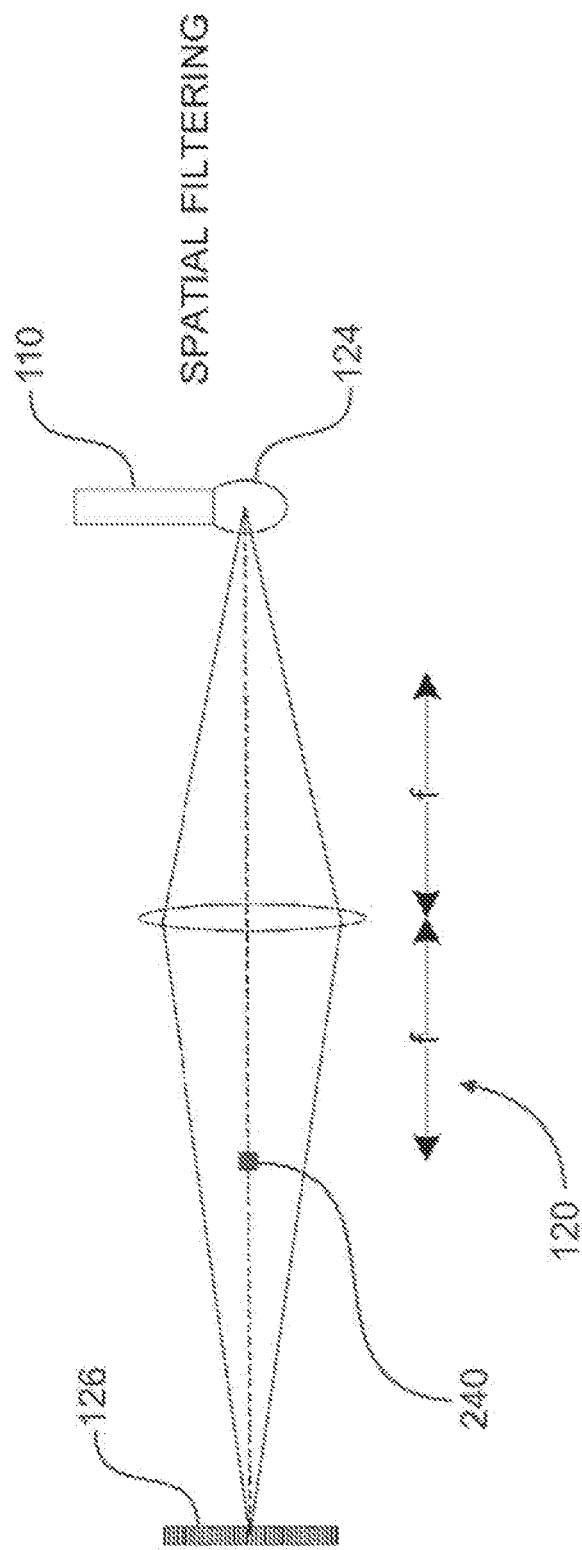

FIG. 15 is a schematic representation of example spatial filtering in pump 100 with an optical imaging system. The goal of high resolution and edge definition for images of drop 124 are attained by illumination techniques, optical techniques, or both, for example, as described supra. In one embodiment, spatial filtering techniques are used in the optics for system 120. For example, mask 240 at the back focal plane of imaging system 102 modifies (via optical Fourier transform) the image generated by the optical system, for example, sensor 126. A DC block filter is shown in FIG. 15. This filter blocks the central cone of the transmitted light and enhances edge images (associated with scattered light).

In one embodiment, the sensitivity of sensor 126 is matched to the illumination spectrum of the light source in system 118. In one embodiment, sensor 126 is a low-cost visible light sensor (400-1000 nm wavelength) and source 122 generates light that is outside the range of human visual perception (i.e., 800-1000 nm). In this case the operator will not be distracted by the bright illumination source.

It should be understood that pump 100 can be any pump mechanism or pump application known in the art and is not limited to only IV infusion pump applications. In the case of a gravity-fed system, the pumping mechanism can be replaced by a valve or flow restrictor, and still be compatible with the configurations and operations described supra.

Thus, it is seen that the objects of the invention are efficiently obtained, although changes and modifications to the invention should be readily apparent to those having ordinary skill in the art, without departing from the spirit or scope of the invention as claimed. Although the invention is described by reference to a specific preferred embodiment, it is clear that variations can be made without departing from the scope or spirit of the invention as claimed.

What is claimed:

1. A method of operating an infusion pump, comprising:
    transmitting light through or around a drop of fluid suspended from an end of a drip tube for the infusion pump, the end of the drip tube located in a drip chamber for the infusion pump, wherein the drip tube is configured for connection to a source of the fluid;
    receiving, using an optical system for the pump, light transmitted through or around the drop;
    transmitting, to a specially programmed microprocessor and using the optical system, data regarding the received light;
    using the microprocessor to calculate a volume of the drop using the data;
    using the microprocessor, generating respective images of the end of the drip tube and the drop from the data;
    locating an apex of the drop, the apex being a portion of the drop at a furthest distance from the end of the drip tube;
    determining, using the location of the apex, an orientation of the drop with respect to the end of the drip tube; and,
    calculating, using the orientation of the drop with respect to the end of the drip tube, an orientation of the drip chamber.

2. The method of claim 1, wherein transmitting light includes: using a telecentric lighting element including a telecentric lens and a first light source, wherein the telecentric lens bundles light rays from the first light source and directs the bundled light rays toward the drop; using a structured lighting element including a second light source and a structural element placed between the second light source and the drop to block or alter light emanating from the second light source; using a pair of laser light sources disposed at an acute angle with respect to each other to generate respective light beams that interact to form an interference pattern; or, transmitting light through a projection lens, the lens having a pattern in or on a surface of the lens, to project the pattern onto the drop.

3. The method of claim 1, further including transmitting, to a specially programmed microprocessor and using the optical system, data regarding the received light; and, calculating, using the processor, a position of a surface of the fluid using the data regarding the received light.

4. The method of claim 3 further comprising using the microprocessor to generate an empty bag alarm or an air-in-line alarm for an instance in which the light transmitted from the light source is not received by the optical system.

5. The method of claim 1 further comprising using the microprocessor to: calculate, using the data, a boundary of the end of the drip tube; and, calculate an orientation of the drop using the boundary as a reference plane.

6. The method of claim 1 further comprising: using the optical system to control illumination properties of light illuminating the end of the drip tube and the drop; and, using the microprocessor to: identify respective boundaries of the end of the drip tube and the drop from the respective images; fit a parametric function to the respective boundaries; and, integrate the parametric function to obtain a volume of the drop.

7. The method of claim 1 further comprising using the microprocessor to: compare the orientation of the drip chamber to a set point; generate an out of bound condition alarm when the orientation equals the set point or varies from the set point by a specified amount, and adjust the infusion pump to correct any deviations between desired and measured flow rates.

8. The method of claim 1, further including using the microprocessor to: generate, from the data, respective images of the drop and of the end of the drip tube; calculate, using the respective images, a boundary of the end of the drip tube; and, calculate a volume, shape, or location of the drop using the boundary as a reference plane.

9. The method of claim 8 further comprising using the microprocessor to: identify a boundary of the drop from the respective images; fit a parametric function to the boundary of the drop; and, integrate the parametric function to obtain a volume of the drop.

10. The method of claim 1, further including using the microprocessor to generate an image of the end of the drip tube from the data; determine, from the image, that a drop is absent from the end of the drip tube for a specified period of time; and, generate an empty bag alarm or an air-in-line alarm.

11. The method of claim 10 further including using the microprocessor to: create a plurality of temporally successive images of the drop from the data; calculate a respective volume for the drop in each successive image; identify changes in the respective volumes; calculate a flow rate of fluid to the output tube based on the changes in the respective volumes, and control the infusion pump accordingly to achieve a desired flow rate.

12. The method of claim 10 further comprising using the microprocessor to: calculate a respective boundary of the drop in each successive image; and, calculate a respective volume for the drop in each successive image by: fitting a parametric function to the respective boundaries of the drop; and, integrating the parametric function to obtain the volume of the drop.

13. The method of claim 10 further comprising using the microprocessor to: create a plurality of temporally successive images of the drop from the data; calculate a respective volume for the drop in each successive image; identify changes in the respective volumes; calculate a flow rate of fluid to the output tube based on the changes in the respective volumes; and, control the pumping mechanism to match the flow rate of fluid with a desired flow rate of fluid.

* * * * *